United States Patent [19]
Nickoloff et al.

[11] Patent Number: 5,354,670
[45] Date of Patent: Oct. 11, 1994

[54] SITE-DIRECTED MUTAGENESIS OF DNA

[75] Inventors: Jac A. Nickoloff, Boston; Frank A. Ray, Brookline; Win P. Deng, Boston, all of Mass.

[73] Assignee: The President and Fellows of Harvard College, Cambridge, Mass.

[21] Appl. No.: 105,761

[22] Filed: Aug. 11, 1993

Related U.S. Application Data

[63] Continuation of Ser. No. 813,581, Dec. 24, 1991, abandoned.

[51] Int. Cl.$^5$ .............................................. C12P 19/34
[52] U.S. Cl. .................................. 435/91.53; 435/6; 435/91.2; 435/91.4; 935/16; 935/17; 935/79; 935/84
[58] Field of Search ................... 435/91.1, 91.53, 91.4, 435/91.2, 6; 935/79, 23

[56] References Cited

FOREIGN PATENT DOCUMENTS 4024187 6/1992 Fed. Rep. of Germany.

OTHER PUBLICATIONS

Marotti et al Gene Anal Techs (1989) 6:67–70.
Nells et al. Gene (1985) 34:315–323.
Rochlitz et al. DNA (1988) 7:515–519.
Lewis et al Nucleic Acids Res (1996) 18:3439–3443.
Pharmacia LKB Biotechnology Products Catalog, 1989.
Higuchi, R. Using PCR to engineer DNA. 1989. In: PCR Technology: Principles and Applications for DNA Amplifications. (H. Erlich, Editor) Stockton Press, New York, N.Y. pp. 61–70.
Kriegler, M. Electroporation. 1990. Gene Transfer and Expression: A Laboratory Manual. Stockton Press, New York, N.Y., pp. 101–102.
Altered Sites® In Vitro Mutagenesis System, (1993) Promega Catalogue p. 138.
International Search Report for International Application No. PCT/US92/11076, completed Feb. 3, 1993, mailed Feb. 23, 1993.
Vandeyar et al. (1988) Gene 65:129–133.
Masumune et al. (1971) J. Biol. Chem. 246:2692–2701.
Nossal (1974) J.Biol. Chem. 249:5668–5676.
Corden et al. (1980) Science 209:1406–1414.
Charles et al. (1982) J. Biol. Chem. 257:7930–7932.
Villafranca et al. (1983) Science 222:782–788.
Gillam et al. (1984) J. Virol. 52:892–896.
Kunkel (1985) Proc. Natl. Acad. Sci. (USA) 82:488–492.
Kunkel et al. (1987) Meth. Enzymol. 154:367–382.
Smith (1985) Ann. Rev. Genet. 19:423–462.
Mandecki (1986) Proc. Natl. Acad. Sci. (USA) 83:7177–7181.
Carter (1987) Meth. Enzymol. 154:382–403.
Zell et al. (1987) EMBO J. 6:1809–1815.
Saiki et al. (1988) Science 239:487–491.
Lewis et al. (1990) Nucleic Acids Res. 18:3439–3443.
Deng et al. (1992) Anal. Biochem. 200:81–88.
Ray et al. (1992) Biotechniques (in press).
Gillam et al. (1985) J. Virol. 53:708–709.

*Primary Examiner*—Margaret Parr
*Assistant Examiner*—Carla Myers
*Attorney, Agent, or Firm*—Lahive & Cockfield

[57] ABSTRACT

This invention pertains to a method of site-specific mutagenesis of DNA. The method can be used to mutagenize DNA, especially circular DNA (for example, virtually any plasmid), requiring only that the DNA carry a nonessential, unique recognition site for a restriction enzyme (restriction site). According to the method, a parental DNA to be mutated, containing a nonessential, unique restriction site, is used to generate progeny DNA containing the desired mutation but lacking the restriction site. The non-mutant parental-type DNA and the mutant progeny DNA are treated with any enzyme that cleaves at the restriction site to cleave the parental-type DNA, leaving the mutant DNA uncleaved. Mutant progeny DNA is selected by transforming cells with the enzyme-treated DNA under conditions such that the cells are transformed with uncleaved DNA at a higher efficiency than cleaved DNA with the result that the majority of transformants carry the mutant DNA. In preferred embodiments, the DNA is circular. The restriction enzyme treatment linearizes parental DNA which retains the nonessential, unique restriction site, leaving mutant DNA which lacks the site circular. Circular DNA transforms host cells more efficiently than linear DNA.

31 Claims, 8 Drawing Sheets

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 27 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE:
        ( A ) NAME/KEY: misc feature
        ( B ) LOCATION: 1..27
        ( D ) OTHER INFORMATION: /label=ampr primer ( x i ) SEQUENCE DESCRIPTION: SEQ ID NO:1:

```
CACCACGATG  CCTGCAGCAA  TGGCAAC                                   27
```

( 2 ) INFORMATION FOR SEQ ID NO:2:

( i ) SEQUENCE CHARACTERISTICS:
        ( A ) LENGTH: 24 nucleoties
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE:
        ( A ) NAME/KEY: misc feature
        ( B ) LOCATION: 1..24
        ( D ) OTHER INFORMATION: /label=EagI primer ( x i ) SEQUENCE DESCRIPTION: SEQ ID NO:2:

```
CAGGTTCTCC  TGCAGCTTGG  GTGG                                      24
```

( 2 ) INFORMATION FOR SEQ ID NO:3:

( i ) SEQUENCE CHARACTERISTICS:
  ( A ) LENGTH: 24 nucleotides
  ( B ) TYPE: nucleic acid
  ( C ) STRANDEDNESS: single
  ( D ) TOPOLOGY: linear ( i i ) MOLECULE TYPE: DNA ( v i i ) IMMEDIATE SOURCE: synthetic ( i x ) FEATURE:
  ( A ) NAME/KEY: misc feature
  ( B ) LOCATION: 1..24
  ( D ) OTHER INFORMATION: /label=AatII primer ( x i ) SEQUENCE DESCRIPTION: SEQ ID NO:3:

GTGCCACCTG TCGACTAAGA AACC                 24

( 2 ) INFORMATION FOR SEQ ID NO:4:

( i ) SEQUENCE CHARACTERISTICS:
    ( A ) LENGTH: 24 nucleotides
    ( B ) TYPE: nucleic acid
    ( C ) STRANDEDNESS: single
    ( D ) TOPOLOGY: linear ( i i ) MOLECULE TYPE: DNA ( v i i ) IMMEDIATE SOURCE:

( i x ) FEATURE:
    ( A ) NAME/KEY: misc feature
    ( B ) LOCATION: 1..24
    ( D ) OTHER INFORMATION:/label=AflIII primer ( x i ) SEQUENCE DESCRIPTION: SEQ ID NO:4:

CAGGAAAGAA GATCTGAGCA AAAG                 24

( 2 ) INFORMATION FOR SEQ ID NO:5:

( i ) SEQUENCE CHARACTERISTICS:
    ( A ) LENGTH: 20 nucleotides
    ( B ) TYPE: nucleic acid
    ( C ) STRANDEDNESS: single
    ( D ) TOPOLOGY: linear ( i i ) MOLECULE TYPE: DNA ( v i i ) IMMEDIATE SOURCE: synthetic ( i x ) FEATURE:
    ( A ) NAME/KEY: misc feature
    ( B ) LOCATION: 1..20
    ( D ) OTHER INFORMATION: /label=AlwNI primer ( x i ) SEQUENCE DESCRIPTION: SEQ ID NO:5:

CTGGCAGCAG CTGGTAACAG                      20

( 2 ) INFORMATION FOR SEQ ID NO:6:

( i ) SEQUENCE CHARACTERISTICS:
    ( A ) LENGTH: 22 nucleotides
    ( B ) TYPE: nucleic acid
    ( C ) STRANDEDNESS: single
    ( D ) TOPOLOGY: linear ( i i ) MOLECULE TYPE: DNA ( v i i ) IMMEDIATE SOURCE: synthetic ( i x ) FEATURE:
    ( A ) NAME/KEY: misc feature
    ( B ) LOCATION: 1..22
    ( D ) OTHER INFORMATION: /label=BsaI primer ( x i ) SEQUENCE DESCRIPTION: SEQ ID NO:6:

TGATACCGCG GGACCCACGC TC                                                                        22

(2) INFORMATION FOR SEQ ID NO:7:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (ii) MOLECULE TYPE: DNA (vii) IMMEDIATE SOURCE: synthetic (ix) FEATURE:
        (A) NAME/KEY: misc feature
        (B) LOCATION: 1..22
        (D) OTHER INFORMATION: /label=EcoRI primer (xi) SEQUENCE DESCRIPTION: SEQ ID NO:7:

CGGCCAGTGA TATCGAGCTC GG                                                                        22

(2) INFORMATION FOR SEQ ID NO:8:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (ii) MOLECULE TYPE: DNA (vii) IMMEDIATE SOURCE: synthetic (ix) FEATURE:
        (A) NAME/KEY: misc feature
        (B) LOCATION: 1..24
        (D) OTHER INFORMATION:/label=HindIII primer (xi) SEQUENCE DESCRIPTION: SEQ ID NO:8:

CAGGCATGCA CGCGTGGCGT AATC                                                                      24

(2) INFORMATION FOR SEQ ID NO:9:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (ii) MOLECULE TYPE: DNA (vii) IMMEDIATE SOURCE: synthetic (ix) FEATURE:
        (A) NAME/KEY: misc feature
        (B) LOCATION: 1..22
        (D) OTHER INFORMATION: /label=ScaI primer (xi) SEQUENCE DESCRIPTION: SEQ ID NO:9:

CTGGTGAGTA TTCAACCAAG TC                                                                        22

(2) INFORMATION FOR SEQ ID NO:10:

(i) SEQUENCE CHARACTERISTICS:
        (A) LENGTH: 29 nucleotides
        (B) TYPE: nucleic acid
        (C) STRANDEDNESS: single
        (D) TOPOLOGY: linear (ii) MOLECULE TYPE: DNA (vii) IMMEDIATE SOURCE: synthetic ( i x ) FEATURE:
    ( A ) NAME/KEY: misc feature
    ( B ) LOCATION: 1..29
    ( D ) OTHER INFORMATION: /label=SspI primer ( x i ) SEQUENCE DESCRIPTION: SEQ ID NO:10:

CTTCCTTTTT CGATATCATT GAAGCATTT                    29

( 2 ) INFORMATION FOR SEQ ID NO:11:

( i ) SEQUENCE CHARACTERISTICS:
        ( A ) LENGTH: 22 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE:
        ( A ) NAME/KEY: misc feature
        ( B ) LOCATION: 1..22
        ( D ) OTHER INFORMATION: /label=XmnI primer ( x i ) SEQUENCE DESCRIPTION: SEQ ID NO:11:

TTGGAAAACG CTCTTCGGGG CG                           22

( 2 ) INFORMATION FOR SEQ ID NO:12:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 1

( x i ) SEQUENCE DESCRIPTION: SEQ ID NO:12:

ACCTGTTTTG CGCAGAAGAA ATG                         23

( 2 ) INFORMATION FOR SEQ ID NO:13:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 2

( x i ) SEQUENCE DESCRIPTION: SEQ ID NO:13:

GAAATGCCAT CTGCTGATGA TGAGGC                    26

( 2 ) INFORMATION FOR SEQ ID NO:14:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 3

( x i ) SEQUENCE DESCRIPTION: SEQ ID NO:14:

ACTCTCAACA TGCTACTCCT CCA                                23

( 2 ) INFORMATION FOR SEQ ID NO:15:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 4B ( x i ) SEQUENCE DESCRIPTION: SEQ ID NO:15:

TTTTGGAGGA GCAGAATGTT GAG                                23

( 2 ) INFORMATION FOR SEQ ID NO:16:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 5

( x i ) SEQUENCE DESCRIPTION: SEQ ID NO:16:

AAGAAATGCC AGCTAGTGAT GAT                                23

( 2 ) INFORMATION FOR SEQ ID NO:17:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 6A ( x i ) SEQUENCE DESCRIPTION: SEQ ID NO:17:

TATCATGTCT GGTACCCCAG GAAGCT                             26

( 2 ) INFORMATION FOR SEQ ID NO:18:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 6B ( x i ) SEQUENCE DESCRIPTION: SEQ ID NO:18:

AGCTTCCTGG GGTACCAGAC ATGATA                             26

( 2 ) INFORMATION FOR SEQ ID NO:19:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 7

( x i ) SEQUENCE DESCRIPTION: SEQ ID NO:19:

GATGATGAAG ACGCCCAGGA AAATGC                  26

( 2 ) INFORMATION FOR SEQ ID NO:20:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 8

( x i ) SEQUENCE DESCRIPTION: SEQ ID NO:20:

AGGCCCCTCA GGCCTCACAG TCT                     23

( 2 ) INFORMATION FOR SEQ ID NO:21:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 9

( x i ) SEQUENCE DESCRIPTION: SEQ ID NO:21:

CCCCTCAGTC CGCACAGTCT GTT                     23

( 2 ) INFORMATION FOR SEQ ID NO:22:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 10B ( x i ) SEQUENCE DESCRIPTION: SEQ ID NO:22:

ATCATGAACA GCCTGTGAGG ACT                     23

( 2 ) INFORMATION FOR SEQ ID NO:23:

( i ) SEQUENCE CHARACTERISTICS:
        ( A ) LENGTH: 23 nucleotides
        ( B ) TYPE: nucleic acid ( C ) STRANDEDNESS: single
( D ) TOPOLOGY: linear ( i i ) MOLECULE TYPE: DNA ( v i i ) IMMEDIATE SOURCE: synthetic ( i x ) FEATURE: primer 11

( x i ) SEQUENCE DESCRIPTION: SEQ ID NO:23:

AAAAACCTCC CGCACCTCCC CCT    23

( 2 ) INFORMATION FOR SEQ ID NO:24:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 12B ( x i ) SEQUENCE DESCRIPTION: SEQ ID NO:24:

ACTCAGCCAC AAGTCTGTAC CAA    23

( 2 ) INFORMATION FOR SEQ ID NO:25:

( i ) SEQUENCE CHARACTERISTICS:
        ( A ) LENGTH: 25 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 13

( x i ) SEQUENCE DESCRIPTION: SEQ ID NO:25:

TGTTTGCTC AAAAGAAATG CCATC    25

( 2 ) INFORMATION FOR SEQ ID NO:26:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 14B ( x i ) SEQUENCE DESCRIPTION: SEQ ID NO:26:

TACCTTTCTC TTGATTTTTG GAGGAG    26

( 2 ) INFORMATION FOR SEQ ID NO:27:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 15B ( x i ) SEQUENCE DESCRIPTION: SEQ ID NO:27:

GGTACTTATA GAGGCTGGGC TCT                                     23

( 2 ) INFORMATION FOR SEQ ID NO:28:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 16B ( x i ) SEQUENCE DESCRIPTION: SEQ ID NO:28:

TTCATGGTAC TCATAGTGGC TGG                                     23

( 2 ) INFORMATION FOR SEQ ID NO:29:

( i ) SEQUENCE CHARACTERISTICS:
        ( A ) LENGTH: 25 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 17

( x i ) SEQUENCE DESCRIPTION: SEQ ID NO:29:

CTCCACACAG GGAAAGAGTG TCTGC                                   25

( 2 ) INFORMATION FOR SEQ ID NO:30:

( i ) SEQUENCE CHARACTERISTICS:
        ( A ) LENGTH: 27 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 18B ( x i ) SEQUENCE DESCRIPTION: SEQ ID NO:30:

TACTAAACAC AACATGACTC AAAAAAC                                 27

( 2 ) INFORMATION FOR SEQ ID NO:31:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 19B ( x i ) SEQUENCE DESCRIPTION: SEQ ID NO:31:

ACTAAACACA GTATGACTCA AAAAAC                                  26

( 2 ) INFORMATION FOR SEQ ID NO:32:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 20

( x i ) SEQUENCE DESCRIPTION: SEQ ID NO:32:

CTCAAATATT TTCCCTGGA ATA        23

( 2 ) INFORMATION FOR SEQ ID NO:33:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: DNA ( v i i ) IMMEDIATE SOURCE: synthetic ( i x ) FEATURE: primer 21A ( x i ) SEQUENCE DESCRIPTION: SEQ ID NO:33:

GTGTCCTGGA AACTTGTAAC AGA        23

SITE-DIRECTED MUTAGENESIS OF DNA

GOVERNMENT SUPPORT

The work leading to this invention was supported by one or more grants from the U.S. government.

RELATED APPLICATIONS

This application is a continuation application of U.S. Ser. No. 07/813,581, filed Dec. 24, 1991, now abandoned.

BACKGROUND OF THE INVENTION

Site-directed mutagenesis is an important procedure in studies of gene expression and protein structure/function relationships. A variety of protocols have been developed to mutate specific bases in plasmid DNA, which employ oligonucleotide primers containing desired mutations flanked by bases complementary to target sequences (reviewed in Smith M. (1985) *Ann. Rev. Genet.* 19:423–462). The primers are usually extended in vitro, although Mandecki (*Proc. Natl. Acad. Sci. U.S.A.* (1986) 83:7177–7181) has described a procedure in which the primers are presumably extended in vivo following transformation of a bacterial host. In the absence of mismatch-repair, DNA replication of heteroduplex DNA is expected to yield mutant products at frequencies of 50% or less. Since actual yields are often much lower than this theoretical maximum, strategies have been developed to select for products derived from the mutant strand. For example, a strategy has been developed by which circular single-stranded DNA (ssDNA) with several uracil bases incorporated in place of thymidine (produced in $dut^-$, $ung^-$ *E. Coli* strains) is used as a template for primer-directed synthesis of a strand carrying the desired mutation. (Kunkel et al. (1987) *Meth. Enzymol.* 154:367–382; Kunkel (1985) *Proc. Natl. Acad. Sci. U.S.A.* 82:488–492). This DNA is transformed into an $ung^+$ strain which degrades the uracil-containing template strand, yielding mutant products at frequencies as high as 98%.

Another strategy is to use two mutagenic primers, one carrying the desired mutation, and the second that reverts a mutation in a selectable marker, such as the ampicillin-resistance ($amp^r$) gene (Lewis et al. (1990) *Nucleic Acids Res.* 18:3439–3443), or gene IV from M13 (Carter (1987) *Meth. Enzymol.* 54:382–403). The two primers direct synthesis of a second strand carrying the reverted selectable marker and the desired mutation. Subsequent selection for the reverted marker yields products carrying the desired mutation at frequencies of about 80%. An analogous strategy couples the primer carrying the desired mutation to a primer that destroys a site recognized by the host restriction/modification system (Carter, ibid.). This strategy permits the efficient recovery of mutant plasmids resistant to the host restriction system. These coupled-primer systems benefit from the use of T4 DNA polymerase for primer extension, rather than the Klenow fragment of *E. coli* DNA polymerase, since the T4 enzyme does not displace the mutagenic primers (Masumune et al. (1971) *J. Biol. Chem.* 246:2692–2701; Nossal (1974) *J. Biol. Chem.* 249:5668–5676). Efficiency is also increased if mismatch repair-defective (mut S) hosts are used, increasing the probability that the reverted selectable marker and the desired mutation cosegregate during the first round of DNA replication (Zell et al. (1987) *EMBO J.* 6:1809–1815).

These specialized mutagenesis procedures impose several requirements. The $dut^-$/$ung^-$ system (Kunkel, ibid.) requires that the target plasmid carry an fl origin of replication, the transformation of the target plasmid into an F, $dut^-$, $ung^-$ host, and the preparation of circular ssDNA templates. Target plasmids must be derivatives of M13, or they must carry fl origins ("phagemids"). ssDNA is produced from phagemids by propagation in the presence of helper phage. Systems that employ revertible selectable markers require subcloning the target DNA into a specialized plasmid vector, and can require specific host strains to permit selection of the reverted marker (Carter, ibid.), or for the production of circular ssDNA templates (Lewis et al., ibid.). If multiple mutations are to be introduced sequentially, revertible marker systems usually require the reintroduction of target DNA fragments into the parent vector carrying the defective marker.

SUMMARY OF THE INVENTION

This invention pertains to a method of site-specific mutagenesis of DNA. The method can be used to mutagenize DNA, especially circular DNA (for example, virtually any plasmid), requiring only that the DNA carry a nonessential, unique recognition site for a restriction enzyme (restriction site). According to the method, a parental DNA to be mutated, containing a nonessential, unique restriction site, is used to generate progeny DNA containing the desired mutation but lacking the restriction site. The non-mutant parental-type DNA and the mutant progeny DNA are treated with an enzyme that cleaves at the restriction site to cleave the parental-type DNA, leaving the mutant DNA uncleared. Mutant progeny DNA is selected by transforming cells with the enzyme-treated DNA under conditions such that the cells are transformed with uncleaved DNA at a higher efficiency than cleaved DNA with the result that the majority of transformants carry the mutant DNA. In preferred embodiments, the DNA is circular. The restriction enzyme treatment linearizes parental DNA which retains the nonessential, unique restriction site, leaving mutant DNA which lacks the site circular. Circular DNA transforms host cells more efficiently than linear DNA.

In one embodiment of the method, two oligonucleotide primers are used, a first oligonucleotide primer which is complementary to the target DNA to be mutated but contains a desired nucleotide mutation of at least one nucleotide, and a second oligonucleotide primer which is complementary and can hybridize to the nonessential, unique restriction site of the same strand but contains at least one nucleotide mutation in the site so that the site is eliminated in the primer (and its complement). The first and second primers are annealed to single-stranded DNA (ssDNA) under conditions which allow the first primer to hybridize to the target DNA and the second primer to hybridize the unique restriction site. A new single strand of DNA is then synthesized on the template of the circular ssDNA and ligated to form a circular double-stranded DNA (dsDNA). The newly synthesized strand lacks the unique restriction site and contains the mutation in the target DNA. A host cell which is repair-mismatch defective is then transformed with the circular dsDNA. Transformed cells are cultured to permit replication and cosegregation of the two mutations in the new strand so that circular dsDNA containing the primer-introduced mutation in both strands is produced. After culturing, circular dsDNA is recovered from the transformed host cells. The recovered DNA is treated with a restriction enzyme that cleaves the nonessential, unique restriction site so that parental DNA in which the restriction site remains is cleaved to form linear DNA, but the DNA lacking the restriction site is not cleaved and remains circular. A second host cell is transformed with the enzyme-treated DNA under conditions which allow circular DNA to be taken up by the cell more efficiently than the cleaved, linear DNA. The transformed cells are cultured and the circular DNA is recovered from the transformed host cell, the majority of the isolated circular dsDNA containing the mutation in the target DNA.

In another embodiment of the invention, a polymerase chain reaction (PCR) can be used to produce a long primer in which the mutation in the target DNA and the mutation eliminating the unique restriction site are linked in a dsDNA fragment. Typically, two primers are used to generate the long primer, but unlike the first embodiment, the primers are complementary to different strands (rather than the same strand) of the circular DNA. The first primer is complementary to the target DNA of one strand of the circular DNA but contains the desired nucleotide mutation. The second oligonucleotide primer is complementary to the nonessential, unique restriction site as it appears in the other strand, but it contains a nucleotide mutation in the site so that the site is eliminated. The circular dsDNA is denatured, and the first and second primers are annealed to the ssDNA under conditions which allow the first primer to hybridize to the target DNA of one strand and the second primer to hybridize the unique restriction site of the other strand. PCR reaction is performed under conditions sufficient to produce a linear dsDNA product (the long primer) containing the mutation in the target DNA but lacking the restriction site. The PCR product is denatured to yield a single-stranded, long primer which is then annealed to the ssDNA circular target DNA, and the remainder of the process is performed as described above.

The method of this invention can also be used for marker gene rescue.

The method of this invention is simple, requires only common materials, and can be rapidly performed (e.g., in as little as 2 days). Circular DNA carrying the mutation of interest can be recovered at high frequencies (generally about 80%). The materials for performing the procedure can be supplied in the form of kits.

BRIEF DESCRIPTION OF THE FIGURES

FIG. 2A shows the structure of pSELneo, and FIG. 2B shows the structure of the plasmid pRSVEd1884;

DETAILED DESCRIPTION OF THE INVENTION

Site directed mutagenesis by unique site elimination (USE) is applicable to virtually any replicable circular DNA. The method is applicable to DNA containing (or made to contain) a nonessential, unique restriction site (i.e. a restriction site which is not essential to the replicability of the DNA and which is present only once in the DNA). This includes plasmid DNA, phagemid DNA, vital DNA, phage DNA and cosmid DNA.

The USE procedure employs two mutagenic oligonucleotide primers. The first primer contains the desired mutation to be introduced into the region of the circular DNA. The primer is the complement of the target DNA of a strand of the circular DNA but contains the desired nucleotide mutation. The second primer is complementary to any nonessential, unique restriction site in the same strand except that it contains a mutation which eliminates the restriction site. The primers can be prepared and phosphorylated by standard procedures.

Figure 1:
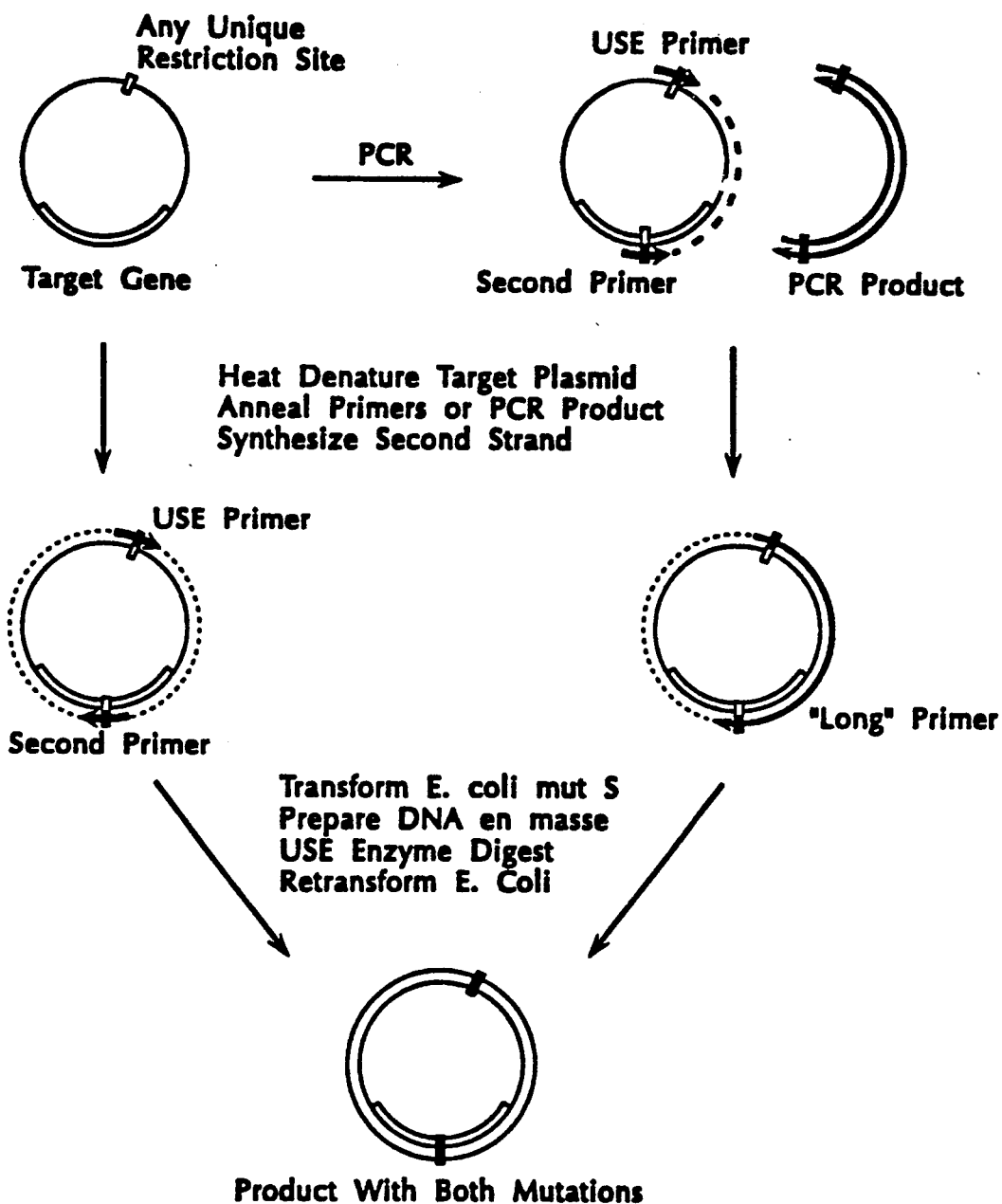
FIG. 1 is a diagrammatic representation of the two stategies for Unique Site Elimination and Long-Primer Unique Site Elimination Mutagenesis.

FIG. 1 (left side) outlines an embodiment of the USE procedure. The two primers are annealed to circular, single-stranded DNA. The annealing can be performed by a quick or slow cooling procedure as described below. Preferably the quick procedure is used.

The annealed primers are used to direct the synthesis of a new complementary strand of DNA containing the two primer-introduced mutations. Primer-directed DNA synthesis of the new strand can be done in an appropriate buffer (e.g. Tris-HCl, pH 7.5) with a DNA polymerase capable of directing second strand DNA synthesis from a primer such as T4 DNA polymerase, a DNA ligase such as T4 DNA ligase, dNTPs and ATP.

The resulting DNA is transformed into a host cell such as the bacterium E. coli. Any E. Coli strain can be used for this transformation step; however, mismatch repair-defective strains such as mut S E. coli are preferable to mismatch repair-proficient strains since mutagenesis efficiencies will be higher. With mismatch repair reduced or eliminated, the two mismatched regions, formed when the two mutagenic primers anneal to the wild-type regions in the target DNA, will not be subject to repair. The two mutations, being in a single-strand, will cosegregate during the first round of DNA replication when the two DNA strands separate.

The transformation is preferably performed by electropotation, but any transformation protocol that yields transformants may be employed. Transformants can be selected en masse in liquid medium containing an appropriate antibiotic.

The circular DNA is recovered from selected transformants, treated with the enzyme that recognizes the nonessential, unique restriction site, and retransformed, preferably by electroporation, into an appropriate host. DNA mutant in the unique restriction site is resistant to digestion, remains circular and transforms bacteria efficiently, while the linearized parental molecule transforms bacteria inefficiently. This differential efficiency of transformation serves as a basis for selecting circular DNA containing the mutation in the unique restriction site. Since this mutation is linked to the desired mutation, the latter can be recovered at frequencies of about 80%.

Nearly all plasmids qualify for the USE procedure because the requirement that target plasmids have a unique, nonessential restriction site is easily fulfilled. Many restriction sites in intergenic regions and polylinkers are effective targets, and unique sites within selectable markers can be mutated by changing bases in "wobble" positions, maintaining both reading frame and coding capacity. Since most plasmids share common vector sequences, few primers, targeted to shared restriction sites, are needed for mutagenizing virtually any plasmid. Since most plasmids are derivatives of pBR322 (Bolivar et al. (1977) *Gene* 2:95-113) or pUC19 (Yanisch-Perron et al. (1985) *Gene* 33:103-119), few USE primers are needed to mutagenize virtually all plasmids. TABLE 1 presents a set of USE primers for common vectors, including pUC19 (Yanisch-Perron, ibid.), pBR322 (Bolivar et al., ibid.), (1977) Gene 2:95-113), pBluescript ™ and pBluescriptII ™ (Stratagene; La Jolla, Calif.), pSP6/T3, pSP6/T7-19, and pT7/T3α-19 (GIBCO BRL; Gaithersberg, Md.), and pTZ19R (Pharmacia; Piscataway, N.J.).

tions in unique restriction sites during second strand synthesis. Mutant plasmids are preferentially recovered because of the marked difference in bacterial transformation efficiencies between circular and linear plasmid DNA. Since selection pressure is imposed only for mutations in the unique site, it is essential that the two mutant primers become linked during in vitro second strand synthesis.

An alternative way of linking two mutagenic primers is to amplify a fragment between two primers by using PCR (Saiki et al. (1988) *Science* 239:487-491), as diagrammed on the right side of FIG. 1. The predominant PCR product consists of double-stranded DNA with the two mutations present in both strands near the ends of the amplified fragment. These PCR products, with linked mutations, can be denatured, annealed to single-stranded target DNA, and can prime second strand synthesis. Thus, the PCR product functions as a long primer with two linked mutations.

Since all double-stranded products of second strand synthesis reactions are expected to carry both mutations in one strand, this procedure, called "Long Primer-USE mutagenesis" (LP-USE), yields products with both mutations more efficiently than USE mutagenesis,

TABLE 1

Unique Site Elimination Primers for Common Vectors

| Target Site | New Site | Codon | Sequence | SEQ ID NO: | Vectors |
|---|---|---|---|---|---|
| AatII | SalI | None | GTGCCACCTGTCGACTAAGAAACC | 3 | 1, 2, 4 |
| AflIII | BglII | None | CAGGAAAGAAGATCTGAGCAAAAG | 4 | 1-6 |
| AlwNI | PvuII | None | CTGGCAGCAG A CTGGTAACAG | 5 | 1-6 |
| BsaI | None | Ser | TGATACCGCGggaCCACGCTC | 6 | 1-6 |
| EcoRI | EcoRV | None | CGGCCAGTGATATCGAGCTCGG | 7 | 1 |
| HindIII | MluI | None | CAGGCATGCACGCGTGGCGTAATC | 8 | 1 |
| ScaI | None | Glu | CTGGTGAGTAttcAACCAAGTC | 9 | 1-6 |
| SspI | EcoRV | None | CTTCCTTTTTCGATATCATTGAAGCATTT | 10 | 1, 2, 4 |
| XmnI | None | Glu | TTGGAAAACGctcTTCGGGGCG | 11 | 1, 3-6 |

In the table, target restriction sites, and newly created sites are given for intergenic and polylinker target sites. Target codons are given for sites in the amp^r gene (lower case letters). Sequences are complementary to the sense strand of the amp^r gene in pUC19. Newly formed restriction sites (or target restriction sites if no new site is formed) are in bold type, and mutant bases are underlined. Vectors are given as follows: 1, pUC19; 2, pBR322; 3, pBluescript and pBluescriptII; 4, pSP6/T3 and pSP6/T7-19; 5, pT7/T3α-19; 6, pTZ19R. The AlwNI primer deletes the nucleotides CCA (Δ). The ECOR1 primer cannot be used if DNA is inserted into the EcoRI or SacI sites. The HindIII primer cannot be used if DNA is inserted into the SphI or HindIII sites. The five italicized bases in the SspI primer are not required if the T to C transition is omitted, but a new EcoRV site will not be created.

Several of these primers convert unique sites into other restriction sites. The newly formed sites can be used to prescreen for mutants with USE mutations, and if the new site is unique, it can be used as a USE target in "cyclic" mutagenesis strategies. Each of the primers in TABLE 1 have at least 10 complementary bases flanking mutagenic bases, and usually they terminate with C or G (Sambrook, J. et al, (1989) *Molecular Cloning: A Laboratory Manual* (2nd. Edition, Cold Spring Harbor Laboratory Press, Cold Spring Harbor, N.Y.).

USE mutagenesis permits the efficient recovery of nonselectable mutations when they are linked to mutawhich depends on the simultaneous annealing of two mutagenic primers to target DNA and a subsequent linkage reaction. In addition, LP-USE may be preferred because both strands of the target DNA are substrates for second strand synthesis since the PCR product carries the two mutations in both strands. Also, target DNA duplexed with long PCR products is more stable than duplexes with oligonucleotide primers.

Reagents for performing the USE or LP-USE mutagenesis procedures can be provided in kits. A kit for USE or LP-USE mutagenesis can comprise the primer designed to eliminate the restriction site, bacterial host strains, preferably including a mismatch repair-defective strain, supplied either as cells competent for transformation or with reagents for producing competent cells and, optionally, the circular DNA (e.g. plasmid) to be mutated (either containing the target DNA or containing appropriate insertion sites for insertion of a target DNA). The kit can also contain a DNA polymerase capable of directing second strand DNA synthesis from a primer, a DNA ligase, deoxyribonucleotides (dNTPs, deoxyadenosine 5'-triphosphate, deoxyguanosine 5'-triphosphate, deoxycytosine 5'-triphosphate, and thymidine 5'-triphosphate), ATP (adenosine-5'-triphosphate), polynucleotide kinase, reagents to enhance DNA synthesis in vitro (e.g. bacteriophage T4 gene 32 protein), a restriction enzyme that recognizes the target unique site and suitable buffers for performing phosphorylation reactions, PCR reactions, DNA synthesis reactions, restriction enzyme digestions and DNA purification. Oligonucleotide primers for introducing mutations into the target DNA or for use in PCR to amplify DNA with a USE primer would normally be provided (synthesized) by the user.

The kit may also contain a control DNA (e.g. plasmid) and control mutagenic primers for monitoring mutagenesis efficiencies. For example, a control DNA can be a plasmid containing a nonessential, unique restriction site and a mutation (e.g. a frameshift mutation) in an indicator gene such as LacZ. A primer for repair of the mutation is included along with the primer for elimination of the restriction site. Typically, the procedure is performed on the control plasmid concurrently with the experimental plasmid to monitor the procedure.

The long primer concept can also be used in methods for rescue of "marker" genes or other target DNA. For this purpose, long primers can be produced from any DNA or RNA which can be subject to PCR. The target DNA (in genomic DNA or in any plasmid, vital DNA, etc.) must be cloned into a DNA vector which is used as the USE template in second-strand synthesis, just as in the mutagenesis procedure. The starting primers for producing the long primer are complementary to the target DNA and flank the region to be rescued. Somewhere in the target DNA, there must be a mutation in a unique restriction site (i.e., unique in the target DNA and in the vector DNA into which the target DNA is cloned). The unique site mutation could be introduced by using a USE primer as a starting primer, for example, but it could occur in any part of the amplified fragment. (In other words, one of the starting primers, or neither or them, could have USE mutations. If neither of the primers have USE mutations, then the targeted genomic DNA, or whatever DNA or RNA is targeted, must have a mutation in some site that is both present and unique in the cloned DNA.) There are no limitations on the second primer as long as it can be used in PCR. The "rescued" target DNA, as described below, will occur between the two primers so that the PCR-amplified fragment contains the rescued region.

The following illustrates the process for a mutant gene in a cell where a wild-type copy of the gene has been cloned into a vector. Primers are annealed to genomic, DNA or RNA, isolated from the cell and used to amplify by PCR the mutant gene. One of the primers is targeted to, and mutates a unique restriction site, e.g., present in DNA flanking the mutant gene. The second primer, used for PCR, anneals to the opposite strand (as usual in PCR), at any position distal to the region under investigation (i.e., the mutant gene to be rescued), but present in the cloned DNA. This PCR fragment is then annealed to denatured vector DNA (or a natural ssDNA if that is the form of the cloned DNA) and LP-USE is performed as described above. Since the PCR fragment contains the marker to rescue linked to the LP-USE mutation in a unique restriction site, when mutants with LP-USE mutations are selected, they will often carry the mutation originally present in the genomic DNA or RNA.

This procedure differs from standard marker rescue since normally, the mutant gene would be cloned by conventional techniques: digesting genomic DNA, inserting fragments into a vector, and screening for correct clones in library (most likely by hybridization); if RNA is used, a cDNA would be produced, inserted into a vector, etc.); if PCR is used, the gene fragment would be amplified, perhaps with new restriction sites added to the ends during PCR, and the fragment would be cloned. LP-USE-based marker rescue has high efficiency and does not require subcloning or difficult screening procedures. This is because USE selection of a mutated (USE mutated) plasmid that has already been cloned is so powerful. Any other DNA that is incorporated into the PCR fragment simply comes along for the ride.

The invention is illustrated further by the following nonlimiting exemplification.

EXAMPLES

A. Methods

1. DNA Manipulations

Plasmids were constructed in vitro by using standard procedures (Sambrook et al., ibid.). DNA was prepared by using a modification of the procedure of Holmes and Quigley (Holmes et al. (1981) Anal. Biochem. 114:193–197): 5 ml LB cultures were grown overnight and the cells were harvested by centrifugation at $3000 \times g$ for 10 min. The cells were suspended in 0.3 ml of sucrose (8%), Triton X-100 (5%), Tris-HCl (50 mM, pH 8.0), and EDTA (50 mM), and 10 μl of lysozyme (10 mg/ml), RNase A (1 mg/ml), and Tris-HCl (50 mM, pH 8.0) (stored at 20° C.) was added. The suspension was briefly mixed, heated to 100° C. for 1 min, and centrifuged at $12,000 \times g$ for 10 min. The cell debris was removed with a toothpick, 10 μl of pronase (10 mg/ml; Sigma Chemical Co.; self-digested for 1 h at 37° C. heated to 80° C. for 2 min and stored at −20° C.) was added to the supernatant, and the solution was incubated at 65° C. for 30 min. Plasmid DNA was precipitated by adding 0.2 ml of 5M ammonium acetate and 1 ml of isopropanol with 1 mM phenylmethylsulfonyl fluoride and incubating at −20° C. for 10 min. DNA was recovered by centrifuging at $12,000 \times g$ for 10 min, and the pellet was rinsed with cold ethanol (80%) and dried. The DNA was suspended in 75 μl of glycerol (2.5%), SDS (0.025%), EDTA (0.5 mM, pH 8.0), bromphenol blue and xylene cyanol FF (0.0125% each). Each sample was heated to 65° C. for 3 min, applied to a 750 μl Sepharose CL-6B (Pharmacia; Piscataway, N.J.) column (prespun at $1500 \times g$ for 2 min) and centrifuged at $1500 \times g$ for 2 min. CL-6B was prepared as a 60% suspension in Tris-HCl (10 mM, pH 8.0) and EDTA (0.5 mM).

Plasmid DNAs were analyzed by agarose gel electrophoresis by using established procedures (Sambrook et al., ibid). DNAs separated by gel electrophoresis were transferred to a Nytran filter (Schleicher and Schuell; Keene, N.H.), and Southern hybridization analysis was performed by using the recommendations of the manufacturer. DNA was labeled with α-[$^{32}$P]-dCTP by random primer extension (Feinberg et al. (1983) Anal. Biochem. 132:6–13).

Figure 2A:
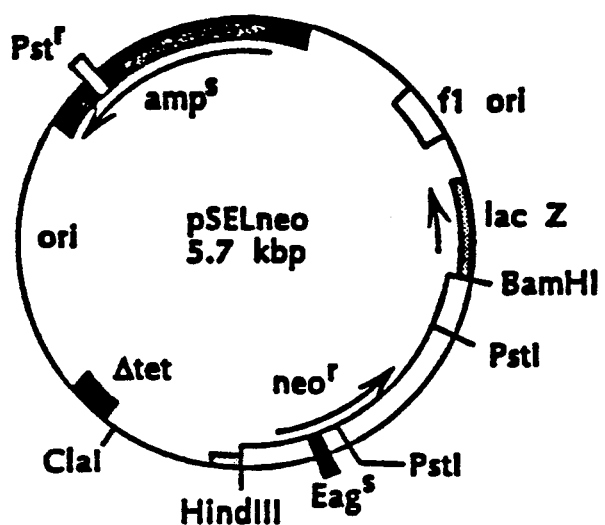
FIGS. 2A and 2B are diagrammatic representations of plasmids used in the Exemplification.

2. Plasmids pSELneo was constructed in two steps. First, a 2.1 kbp HindIII/BamHI fragment carrying the neomycin gene from pSV2neo (Southern et al. (1982) J. Mol. Appl. Genet. 1:327–341) was inserted into the polylinker of pSELECT-1 (Promega Corp.; Madison, Wis.), producing pWPD1. pWPD1 is resistant to tetracycline and kanamycin, but sensitive to ampicillin because of a deletion of the PstI site in the amp$^r$ gene. The tetracycline-resistance gene of pWPD1 was deleted in the second step by digesting pWPD1 with EcoRV and AccI, filling-in the AccI site with T4 DNA polymerase, and recircularizing with T4 DNA ligase. The resulting plasmid, called pSELneo, is kanamycin-resistant (kan$^r$), ampicillin-sensitive (amp$^s$), tetracycline-sensitive, and has a unique EagI site. The structure of pSELneo is shown in FIG. 2A. Cleavable restriction sites are shown by black lines. The deleted PstI site, shown by the open line, is resistant to digestion by PstI (PstI$^r$). Defective genes are shaded or black and functional genes are white.

Figure 2B:
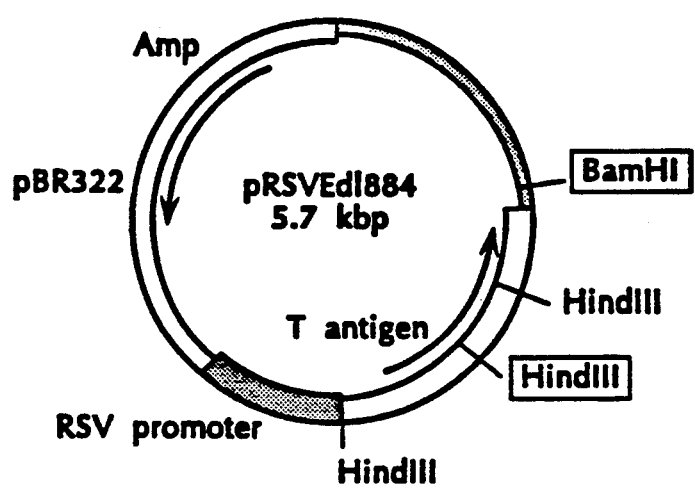

Another target plasmid, pRSVEd1884 is shown in FIG. 2B. This plasmid is a 5.7 kbp derivative of SV40 and pRSVcat with the coding region for SV40 large T antigen driven by the rous sarcoma virus promoter. DNA sequence analysis of double-stranded plasmid DNA was performed by using Sequenase version 2.0 (U.S. Biochemical Corp., Cleveland, Ohio) as recommended by the manufacturer.

3. Synthesis and Phosphorylation of Primers

Primers were synthesized on a Biosearch model 8700 DNA synthesizer (Novato, Calif.) using phosphoramidite chemistry. Following deprotection of primers, the solutions were evaporated, the DNA was rinsed with 0.5 ml ethanol, evaporated, and resuspended in 0.2 ml dH$_2$O. The solutions were centrifuged at 12,000×g for 10 min, and the supernatants were recovered. Primers were used without further purification. The concentrations of primer solutions were determined spectrophotometrically.

Phosphorylations were performed by incubating primers (100 pmole), 70 mM, Tris-HCl, pH 7.6, MgCl$_2$ (10 mM), DTT (5 mM), 0.1 mM, ATP, and T4 polynucleotide kinase (10 units; New England Biolabs; Beverly, Mass.) in a volume of 20 μl for 2 h at 37° C.

Two mutagenic primers that were synthesized are shown in TABLE 2.

TABLE 2 amp$^r$ primer:
  5'-CACCACGATGCCTGCAGCAATGGCAAC-3'

TABLE 2-continued

EagI$^r$ primer:
  5'-CAGGTTCTCCTGCAGCTTGGGTGG-3'

The "amp$^r$" primer (SEQ ID NO:1) restores ampicillin-resistance to pSELneo by recreating the deleted PstI site. The new PStI site is in bold type, and the mutant bases are underlined. The EagI$^r$ primer (SEQ ID NO:2) converts the unique EagI site in the neomycin gene to a PstI site, producing EagI-resistant (EagI$^r$) plasmids. The mutations introduced by the EagI$^r$ primer do not alter the coding capacity of the neomycin gene, and thus both mutant and nonmutant products are kan$^r$.

Twenty-two additional mutagenic primers (SEQ ID NOS:12-33) that were synthesized, including two that were complementary to the region flanking the unique BamHI site in pRSVEd1884 (primers 6A (SEQ ID NO:17) and 6B (SEQ ID NO:18)), are shown in TABLE 3.

TABLE 3

Mutagenic Primers

| Primer | Target | Sequence | SEQ ID NO. | Procedure |
|---|---|---|---|---|
| 1 | Ser$_{106}$→Ala | ACCTGTTTGCGCAGAAGAAATG | 12 | USE/LP-USE |
| 2 | Ser$_{112}$→Ala | GAAATGCCATCTGCTGATGATGAGGC | 13 | LP-USE |
| 3 | Ser$_{123}$→Ala | ACTCTCAACATGCTACTCCTCCA | 14 | USE |
| 4B | Thr$_{124}$→Ala | TTTTGGAGGAGCAGAATGTTGAG | 15 | USE |
| 5 | Ser$_{111}$→Ala | AAGAAATGCCAGCTAGTGATGAT | 16 | USE |
| 6A | BamHI | TATCATGTCTGGTACCCCAGGAAGCT | 17 | USE |
| 6B | BamHI | AGCTTCCTGGGGTACCAGACATGATA | 18 | USE/LP-USE |
| 7 | Ser$_{639}$→Ala | GATGATGAAGACGCCCAGGAAAATGC | 19 | LP-USE |
| 8 | Ser$_{676}$→Ala | AGGCCCCTCAGGCCTCACAGTCT | 20 | LP-USE |
| 9 | Ser$_{677}$→Ala | CCCCTCAGTCCGCACAGTCTGTT | 21 | USE |
| 10B | Ser$_{679}$→Ala | ATCATGAACAGCCTGTGAGGACT | 22 | USE |
| 11 | Thr$_{701}$→Ala | AAAAACCTCCCGCACCTCCCCCT | 23 | USE/LP-USE |
| 12B | Pro$_{584}$→Leu | ACTCAGCCACAAGTCTGTACCAA | 24 | USE |
| 13 | Glu$_{107}$→Lys | TGTTTTGCTCAAAAGAAATGCCATC | 25 | USE/LP-USE |
| 14B | Lys$_{128}$→Ile | TACCTTTCTCTTGATTTTTGGAGGAG | 26 | USE |
| 15B | His$_{313}$→Leu | GGTACTTATAGAGGCTGGGCTCT | 27 | USE |
| 16B | Lys$_{315}$→Glu | TTCATGGTACTCATAGTGGCTGG | 28 | USE |
| 17 | His$_{203}$→Glu | CTCCACACAGGGAAAGAGTGTCTGC | 29 | USE/LP-USE |
| 18B | Ala$_{149}$→Val | TACTAAACACAACATGACTCAAAAAAC | 30 | USE |
| 19B | Ala$_{149}$→Thr | ACTAAACACAGTATGACTCAAAAAAC | 31 | USE |
| 20 | Pro$_{522}$→Ser | CTCAAATATTTTCCCCTGGAATA | 32 | USE |
| 21A | HindIII | GTGTCCTGGAAACTTGTAACAGA | 33 | LP-USE/USE |

In TABLE 3, Target codons and codon positions within the T antigen gene are given for each primer. Mutant bases within primers are underlined. Primers 6A (SEQ ID NO:17) and 6B (SEQ ID NO:18) were used to introduce selectable mutations in the BamHI site. These primers destroy the BamHI site by converting it to a KpnI site. The remaining primers (SEQ ID NOS:12-16 and 19-33) were designed to introduce mutations into various regions of the large T antigen gene.

4. Site-Directed Mutagenesis by USE

Mutagenesis of pSELneo was performed as follows. A 20 μl solution containing either one or both phosphorylated primers (25 pmoles; 0.2 μg), pSELneo (0.025 pmoles; 0.1 μg), Tris-HCl (20 mM, pH 7.5), MgCl$_2$ (10 mM), and NaCl (50 mM) was heated to 100° C. for 3 min. Primers were annealed by either immediately placing the tubes containing the annealing mixtures in an ice bath (quick cooling) or by incubating tubes for 10 min at 25° C., and then placing them in an ice bath (slow cooling). Primer-directed DNA synthesis was performed by adding 3 μl of a solution containing Tris-HCl (100 mM, pH 7.5), dNTPs (5 mM each), ATP (10 mM), and DTT (20 mM), 5 μl of dH₂O, 1 μl of T4 DNA polmerase (3 units, New England Biolabs), and 1 μl of T4 DNA ligase (400 units, New England Biolabs). The reaction was incubated at 37° C. for 90 min, then stopped by adding 3 μl of a solution containing SDS (0.25%) and EDTA (5 mM, pH 8.0) and heating to 65° C. for 5 min. The DNA was purified by spin column chromatography through Sepharose CL-6B. Two μl of the eluate was used to transform *E. coli* strain BMH 71-18 mut S (Zell et al. (1987) *EMBO J.* 6:1809–1815) by electropotation using a Gene Pulser (Biorad; Richmond, Calif.) according to the manufacturer's recommendations.

Following electropotation, the cells were resuspended in 1 ml of SOC medium (Sambrooket et al., ibid.), and incubated at 37° C. for 1 h. To determine the number of primary BMH 71-18 mut S transformants, aliquots of this solution were plated onto LB agar plates containing either ampicillin (100 μg/ml) or kanamycin (40 μg/ml). Five ml of LB containing either ampicillin or kanamycin was added to the remaining cells, and the cell suspensions were incubated overnight at 37° C. Plasmid DNAs were prepared from the 5 ml cultures as described above, and 0.5 μg quantities were digested with EagI (5 units, New England Biolabs) in 20 μl volumes, or were not treated. Both digested and undigested DNAs were purified by CL-6B spin column chromatography prior to electropotation into *E. coli* strain DH5α. The transformed cells were plated on LB plates containing the same antibiotic used to select the original BMH 71-18 mut S transformants and incubated at 37° C. overnight. Mutant plasmids, prepared from amp$^r$ or kan$^r$ colonies as described above, were identified by digesting with EagI or with PstI and ClaI. When the amp$^r$ primer was used and no selection pressure for amp$^r$ mutants was applied during the mutagenesis procedures, amp$^r$ mutants were identified by replica-plating kan$^r$ transformants to LB plates containing ampicillin.

Specific mutations were introduced into plasmid pRSVEd1884 by using USE mutagenesis as described by Deng et al. *Anal. Biochem.* (1992) (in press), or by using LP-USE mutagenesis as follows. "Long primers" were produced in 30-cycle PCR reactions by using standard conditions (see, e.g. Sambrook et al., ibid.). amplified fragments were purified by Cl-6B spin column chromatography (Pharmacia, Piscataway, N.J.) as described by Deng et al., (ibid.), and PCR product concentrations were estimated by using agarose gel electrophoresis with a standard solution of phage λ DNA digested with HindIII.

Approximately 100 pmol of PCR product was phosphorylated by using T4 polynucleotide kinase and ATP (see, e.g., Sambrook et al., ibid.). One-fourth of the phosphorylated PCR product was mixed with 0.025 pmol of target plasmid in solutions containing 20 mM Tris-HCl, pH 7.5, 10 mMMgCl₂, and 50 mM NaCl. Mixtures were heated to 100° C. for 3 min to denature the target plasmid and PCR product, then quickly cooled to 4° C. The DNAs were annealed for 30 min at room temperature, then second-strand synthesis was performed by adding 3 μl of a solution containing 100 mM Tris-HCl (pH 7.5), 5 mM of each dNTP, 10 mM ATP, and 20 mM DTT, 2.5 μl of T4 DNA ligase (1000 units), and 1 μl T4 DNA polymerase (3000 units). Synthesis was performed for 5–30 min at 37° C. before reactions were stopped with 3 μl of a solution containing 0.25% SDS and 5 mM EDTA (pH 8.0) and heated to 65° C. for 5 minutes. The DNA was purified by spin column chromatography through Sepharose CL-6B as described by Deng et al. (ibid.). *E. coli* strain BMH 71-18 mut S (Zell et al. (1987) *EMBO J.* 6:1809–1815) was transformed with 2 μl of the eluate by using a Gene Pulser (Bio-Rad; Richmond, Calif.) according to the manufacturer's recommendations. The remaining steps (growth of BMH mut S transformants en masse, digestion of plasmid DNA, and transformation of *E. coli* strain DH5α) were performed as described above, except that second strand synthesis reactions were performed for 5 to 30 min.

B. Results

1. Experimental Design

Figure 3:
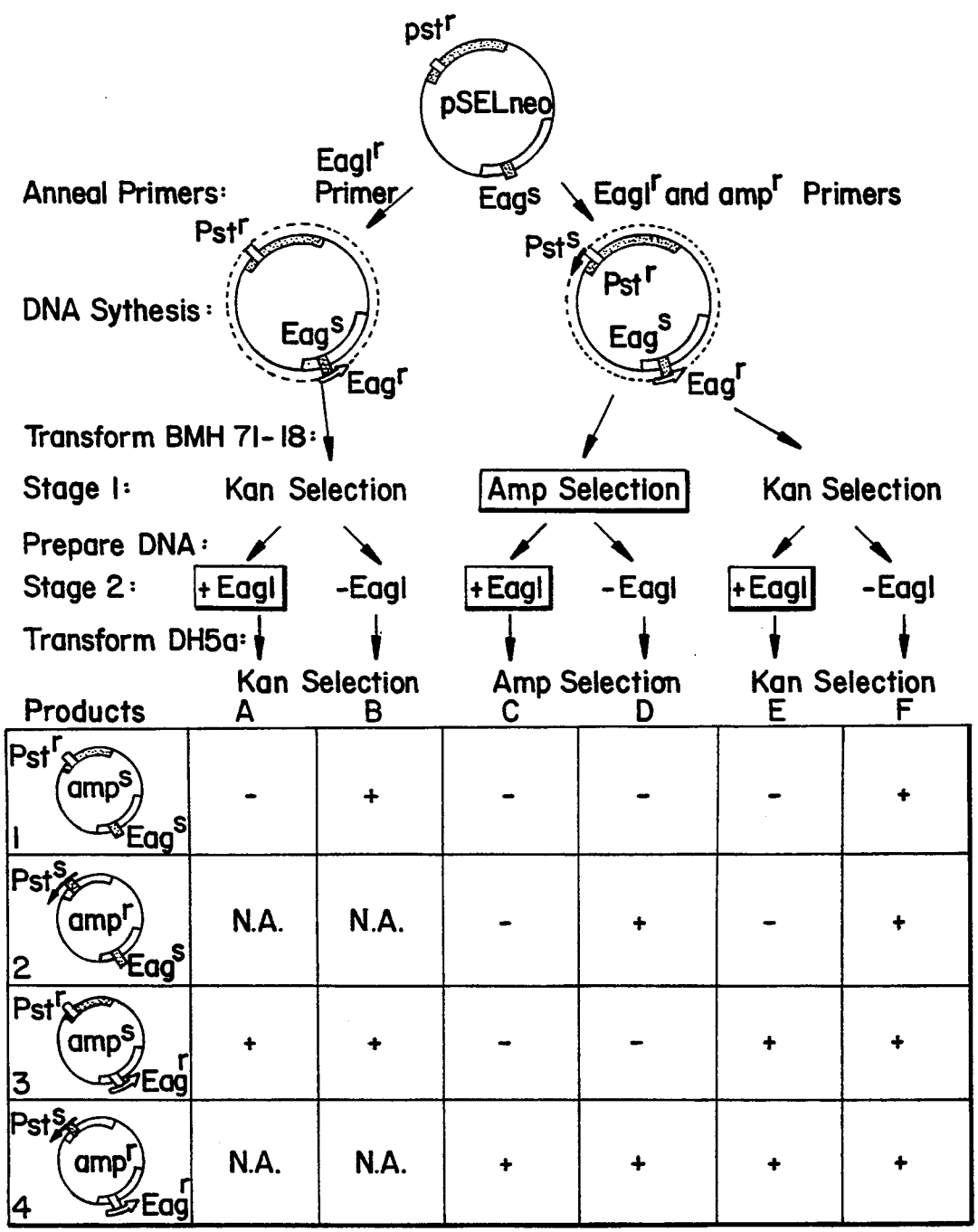
FIG. 3 shows six schemes for mutagenesis of pSELneo.

The pSELneo plasmid was mutagenized by using each of the six schemes diagrammed in FIG. 3. Defective genes are shaded or black, and functional genes are white. Six different schemes (A-F) are shown. The amp$^r$ primer (SEQ ID NO:1, black arrow) repairs the amp$^r$ gene, and restores the PStI site, creating a PstI-sensitive site, PstI$^s$. The EagI$^r$ primer (SEQ ID NO:2, white arrow) eliminates the unique EagI site, creating an EagI$^r$ site by converting it into a PstI site. Primer-directed DNA synthesis produces the second DNA strand. BMH 71-18 mut S transformants were selected by using either ampicillin or kanamycin medium. Growth in ampicillin medium constitutes stage 1 selection for amp$^r$ mutants (shaded box). Since the EagI$^r$ mutation does not alter the neo reading frame, growth in kanamycin medium selects transformants but not mutants. Digesting the resulting DNA with EagI constitutes stage 2 selection for EagI$^r$ mutants (schemes A, C, and E; shaded boxes). Predicted outcomes for each mutagenesis procedure are shown in the table at the bottom of FIG. 3. Minus signs indicate selection pressure against particular products. Plus signs indicate that products are recoverable, but not necessarily selected; shaded boxes indicate selected products. Since no selective pressure was applied in procedure F, all products are recoverable but none are selected. When the EagI$^r$ primer is used alone (schemes A and B), amp$^r$ products cannot be formed (boxes marked N.A., not applicable).

When only the EagI$^r$ primer (SEQ ID NO:2) was annealed to pSELneo, BMH 71-18 mut S transformants were selected by growth in kanamycin medium (FIG. 3, schemes A and B). When both primers were employed, transformants were selected either by growth in ampicillin medium, which selects for amp$^r$ mutants (stage 1 selection; FIG. 3, schemes C and D), or by growth in kanamycin medium. In the latter case there was no selective pressure for amp$^r$ plasmids (i.e., no stage 1 selection, FIG. 3, schemes E and F).

Plasmid DNA was isolated following growth of BMH 71-18 mut S transformants en masse. At this point, selection for EagI$^r$ mutants could be imposed by treating the DNA with EagI before transforming DH5α (FIG. 3; "stage 2 selection"). Treatment with EagI linearizes EagI-sensitive (EagI$^s$) wild-type plasmids, reducing their ability to transform *E. coli*. The mutant, EagI$^r$ plasmids, remain circular and transform *E. coli* efficiently. By omitting the EagI digestion, both EagI$^r$ and wild-type (EagI$^s$) plasmids are recoverable. It is important to differentiate between procedures that "select for transformants," from those that "select for mutants." For example, although BMH 71-18 mut S transformants can be "selected" by growth in kanamycin medium, this procedure does not impose selective pressure for amp$^r$ or EagI$^r$ mutants. Mutants were selected by growing transformants in ampicillin medium at stage 1 (when applicable) and/or by digesting DNAs with EagI at stage 2.

2. Mutagenesis of pSELneo

To determine whether circular double-stranded DNA is an effective starting material for site-directed mutagenesis, pSELneo was mutagenized by using either the EagI$^r$ primer (SEQ ID NO:2) or both the EagI$^r$ (SEQ ID NO:2) and amp$^r$ (SEQ ID NO:1) primers (FIG. 3, schemes A–D). Primers were annealed to pSELneo either slowly or quickly as described above. BMH 71-18 mut S transformation efficiencies were determined by plating aliquots of transformed cells on LB plates containing kanamycin, and mutagenesis by the amp$^r$ primer was assayed by plating aliquots on ampicillin plates. The results are shown in TABLE 4 below.

TABLE 4

| | Mutagenesis of Circular Double-Stranded DNA | | | |
|---|---|---|---|---|
| | Expt 1 | | Expt 2 | |
| selection | slow | quick | slow | quick |
| Kanamycin | 2280 | 2418 | 1320 | 2100 |
| Ampicillin | 124 | 213 | 30 | 50 | pSELneo was mutagenized as described in Materials and Methods. Aliquots of BMH 71-18 mut S transformants were plated on LB plates containing either 40 μg/ml kanamycin or 100 μg/ml ampicillin, to determine the number of transformants or mutants, respectively. The total number of primary kan$^r$ or amp$^r$ transformants for two experiments are given.

amp$^r$ mutants were readily obtained when the amp$^r$ primer (SEQ ID NO:1) was included (FIG. 3, scheme C), indicating that circular double-stranded DNA is an effective starting material for mutagenesis. Without this primer, no amp$^r$ products were recovered. Although both slow and quick annealing procedures were effective, quick annealing yielded about two-fold more amp$^r$ mutants.

3. Efficiencies of USE Mutagenesis

The efficiencies of EagI$^r$ mutagenesis were compared when selective pressures were applied for resistance to antibiotics (stage 1), enzymatic digestion (stage 2), or both. Stage 1 selection was applied when both primers were employed (FIG. 3, schemes C and D), and omitted when the EagI$^r$ primer (SEQ ID NO:2) was used alone (FIG. 3, schemes A and B). Plasmid DNA isolated from overnight cultures of BMH 71-18 mut S transformants was treated with EagI (stage 2 selection; FIG. 3, schemes A and C) or was left untreated (FIG. 3, schemes B and D), before being transformed into DH5α. Since DH5α transformants were plated on LB plates containing the same antibiotic used to select the original BMH 71-18 mut S transformants, there was no additional selective pressure for amp$^r$ mutants during the DH5α transformation step.

Both EagI-digested and undigested samples were examined by using agarose gel electrophoresis. Since some samples had no detectable circular DNA in the ethidium bromide-stained gel, [$^{32}$P]-labelled pSELneo was hybridized to a Southern blot of these DNAs. The procedure and results are summarized in FIG. 4. As shown in the top portion of FIG. 4, DNAs were isolated from BMH 71-18 mut S transformants following either slow (S) or quick (Q) annealing procedures. These DNAs were treated with EagI (+) or were not treated (−).

Stage 1 selection for amp$^r$ mutants was applied to cells giving rise to the DNAs in lanes 1–4, but not lanes 5–8. DNAs were separated on a 0.8% agarose gel, transferred to a Nytran filter (Schleicher and Schuell; Keene, N.H.), and hybridized to [$^{32}$P]-labeled pSELneo. Autoradiography was performed for 30 minutes at room temperature. Nicked circular, linear, and supercoiled forms migrate to the indicated positions.

Figure 4:
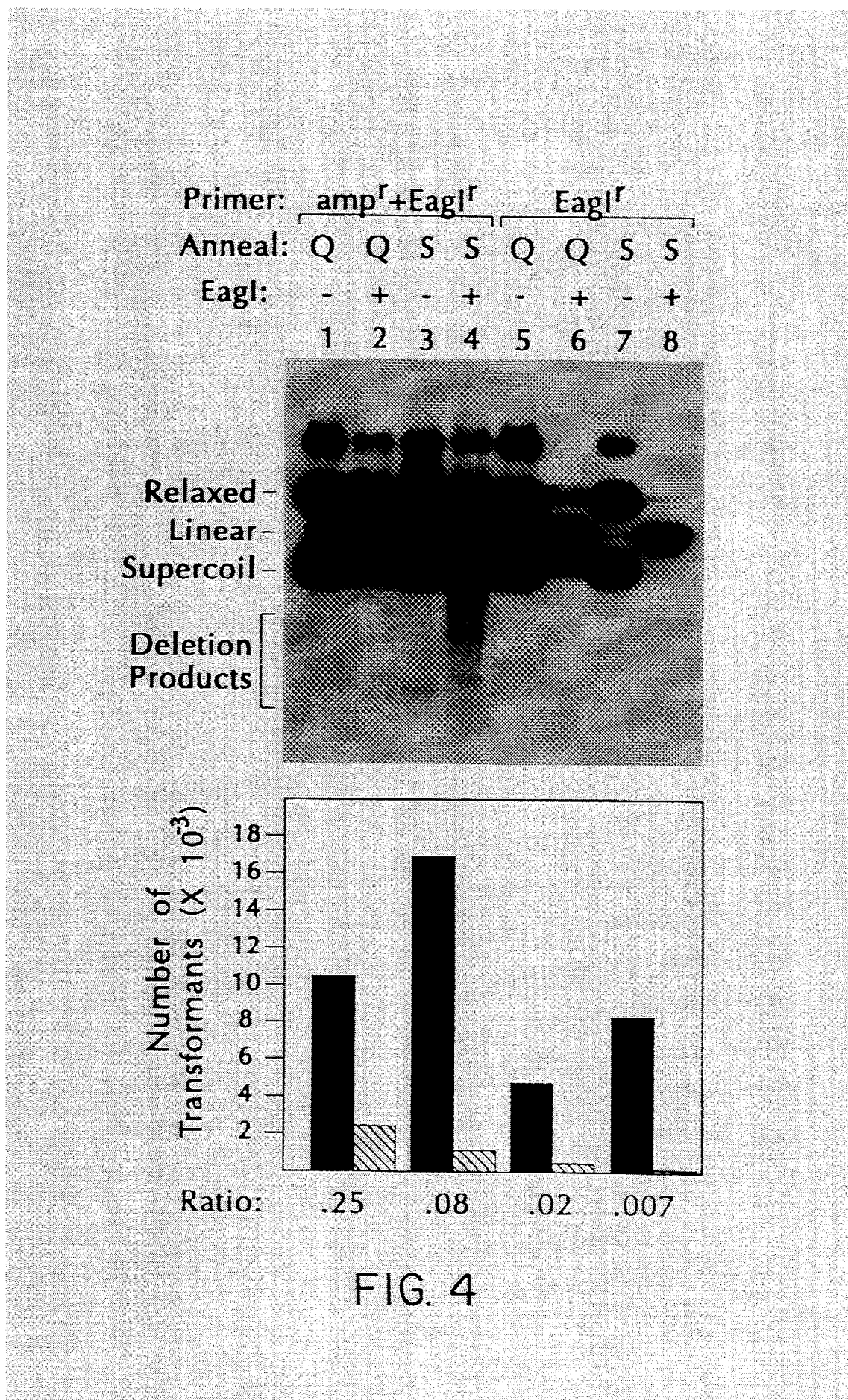
FIG. 4 shows the characterization of plasmid DNA isolated from BMH 71-18 rout S transformants.

The bottom portion of FIG. 4 describes the transformation of DH5α. Aliquots of each DNA above were transformed into DH5α, and the number of transformants obtained ($\times 10^{-3}$) is shown. The ratio of the number of transformants obtained with EagI-treated versus untreated samples for each DNA is given below.

Greater quantities of circular DNA were present after EagI digestion when stage 1 selective pressure for amp$^r$ mutations was applied, a result that is consistent with the idea that the nonselected EagI$^r$ mutations were often coupled with the stage 1-selected amp$^r$ mutation (FIG. 4; compare lane 2 with lane 6, and lane 4 with 8). More DNA isolated from BMH 71-18 mut S cultures was EagI$^r$ with quick annealing than with slow annealing, and this difference was apparent with or without first stage selection.

As expected, DH5α transformation efficiencies were proportional to the amount of circular DNA in each sample. These results parallel those described above, suggesting that quick annealing is a more effective mutagenesis procedure than slow annealing.

Figure 5:
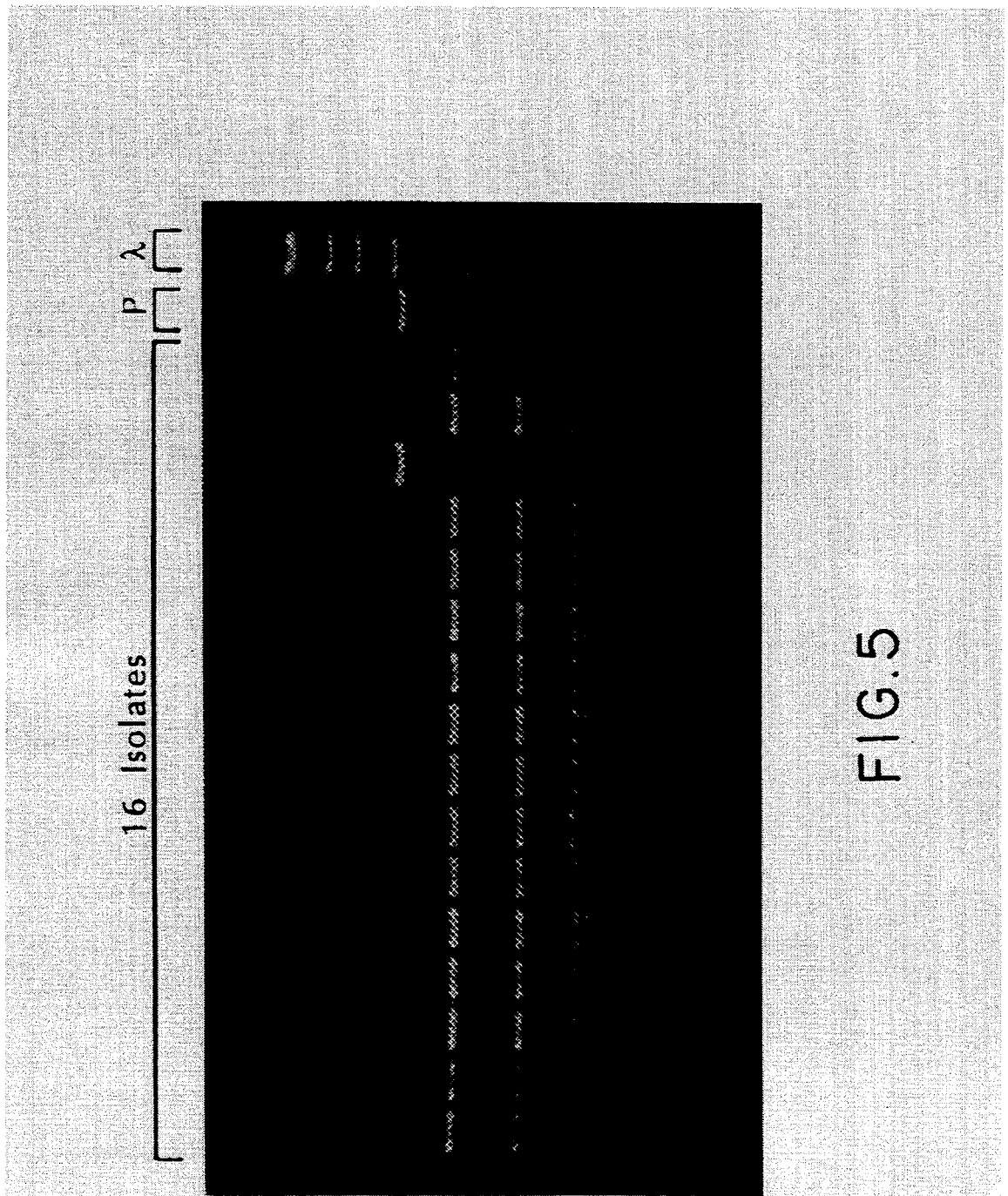
FIG. 5 shows the characterization of mutant plasmids following Unique Site Elimination mutagenesis.

Each of four mutagenesis procedures (FIG. 3, schemes A–D) were performed in two ways by using either slow or quick annealing. Plasmid DNAs from 16 DH5α transformants from each mutagenesis procedure were digested with PstI and ClaI, run on a 0.8% agarose gel, stained with ethidium bromide, and photographed. The parent plasmid has two PstI sites and one ClaI site, yielding a 4.1 kbp fragment and two comigrating fragments. The amp$^r$ primer introduces a PstI site into the 4.1 kbp fragment producing 2.9 kbp and 1.2 kbp fragments. The EagI$^r$ primer introduces a PstI site into one of the comigrating fragments, producing a 140 bp fragment (not visible) and a second fragment that runs slightly faster than the comigrating fragments. The results of these experiments are summarized in TABLE 5. Plasmid DNAs from 16 DH5α transformants (from scheme C, FIG. 3) and pSELneo (lane "P"), analyzed as described above, are presented in FIG. 5. λ DNA digested with HindIII was run in the lane marked "λ". All 16 isolates carry the new PstI site in the neomycin gene, although one has a small deletion. Fifteen of 16 have new PstI sites in the amp$^r$ gene, even though all 16 confer resistance to ampicillin.

In some cases, isolated DNAs contained mixtures of mutant and parental plasmids. Since it is relatively easy to isolate a mutant plasmid from these mixtures by retransforming E. coli, the mixed isolates are included in the calculation of mutagenesis frequencies in TABLE 5.

TABLE 5

Recovery of EagI<sup>r</sup> Mutants

| Set | Primers | Selections | Anneal | Correct | Mixed | Frequency |
|---|---|---|---|---|---|---|
| 1 | EagI<sup>r</sup> | None | Slow | 0 | 0 | 0% |
| 2 | EagI<sup>r</sup> | None | Quick | 0 | 0 | 0% |
| 3 | EagI<sup>r</sup> | Stage 2 | Slow | 12 | 0 | 75% |
| 4 | EagI<sup>r</sup> | Stage 2 | Quick | 14 | 0 | 88% |
| 5 | EagI<sup>r</sup> + amp<sup>r</sup> | Stage 1 | Slow | 7 | 2 | 56% |
| 6 | EagI<sup>r</sup> + amp<sup>r</sup> | Stage 1 | Quick | 10 | 3 | 81% |
| 7 | EagI<sup>r</sup> + amp<sup>r</sup> | Stage 1 & 2 | Slow | 8 | 1 | 56% |
| 8 | EagI<sup>r</sup> + amp<sup>r</sup> | Stage 1 & 2 | Quick | 15 | 0 | 94% |

One or both mutagenic primers were annealed to pSELneo either quickly or slowly. amp<sup>r</sup> mutants were selected during stage 1 by growing BMH 71-18 mut S transformants in ampicillin medium; EagI<sup>r</sup> mutants were selected during stage 2 selection by digesting DNA isolated from BMH 71-18 mut S transformants with EagI. Sixteen isolates from each set were mapped with EagI and with PstI/ClaI. The number of isolates with EagI<sup>r</sup> plasmids (Correct), or mixtures of EagI<sup>r</sup> and EagI<sup>s</sup> plasmids (Mixed) are given. The EagI<sup>r</sup> mutagenesis frequency was calculated as the sum of the Correct and Mixed isolates divided by 16 and expressed as a percentage (Frequency).

With both first and second stage selections, 14 of 16 isolates carried both mutations when the quick annealing procedure was used, while slow annealing yielded only 9 of 16 with both mutations. Interestingly, most of the incorrect products isolated following slow annealing resulted from deletion events. These deletion products are visible in the lower region of the autoradiograph shown in FIG. 4. Few deletion products were isolated under quick annealing conditions, and none were detected by Southern hybridization analysis when quick annealing was used (FIG. 4), even when autoradiography times were extended.

About 80% of the recovered products carried the EagI<sup>r</sup> mutation when either stage 1 or stage 2 selection was applied (TABLE 5), indicating that a single selective pressure is sufficient to permit the recovery of EagI<sup>r</sup> mutants at high frequency. These results further indicate that the selection pressure for plasmids lacking a unique restriction site is strong enough to permit their efficient recovery, and suggest that it may be possible to recover nonselected mutations with high efficiency if they are linked to a selectable mutation in a unique restriction site.

The experiments diagrammed in FIG. 3, schemes E and F, were performed to test whether the selection for the elimination of a unique site can be used to recover nonselected mutations with high efficiency. In these experiments, the roles of the amp<sup>r</sup> and EagI<sup>r</sup> mutations were reversed, that is, EagI<sup>r</sup> mutants were selected by digesting with EagI prior to transforming DH5α (FIG. 3, scheme E), and amp<sup>r</sup> mutants were not selected (all transformants were grown in kanamycin medium). In the control experiment (FIG. 3, scheme F), no mutant selections were imposed. Plasmids carrying amp<sup>r</sup> mutations were identified by replica plating a minimum of 100 kan<sup>r</sup> transformants to LB medium containing ampicillin. In two independent experiments, 80% of the kan<sup>r</sup> transformants were amp<sup>r</sup> when EagI-selective pressure was applied. Without selective pressure, the amp<sup>r</sup> mutation was recovered at a frequency of about 5%. Thus, mutagenesis by USE is an effective protocol for recovering nonselected mutations.

4. Mutagenesis of pRSVEd1884 with USE and LP-USE

To compare the efficiencies of USE and LP-USE mutagenesis, identical mutations were introduced into plasmid pRSVEd1884 by using three mutagenic primers, including two complementary primers that eliminate the unique BamHI site by converting it to a KpnI site (primers 6A and 6B, TABLE 3). The third primer (21A, TABLE 3) introduces a silent mutation into the T antigen gene, destroying one of three HindIII sites in pRSVEd1884. Pairing primer 21A with primer 6A produces linked mutations in BamHI and HindIII sites during second strand synthesis with USE mutagenesis. Pairing primer 21A with primer 6B in a PCR reaction produces a 1469 bp fragment with linked BamHI and HindIII mutations that can be subsequently used for LP-USE mutagenesis. These pairs of primers were chosen for initial tests since the mutations produced are easily identified by restriction mapping, facilitating the analysis of candidate plasmids.

LP-USE mutagenesis was performed as described above. Besides the addition of the PCR amplification step, the only significant difference between the USE and LP-USE procedures concerned the length of time that second strand synthesis reactions were allowed to proceed. Second strand synthesis reactons were incubated for 30 min with USE, and from 5 to 30 min with LP-USE. Following electroporation into E. Coli strain BMH 71-18 mut S (Zell et al. (1987) EMBO J. 6:1809–1815), 10% of the transformed cells were plated on LB agar plates with ampicillin to allow an estimation of the number of primary transformants. The remaining transformants were expanded en masse by overnight growth in 5 ml of LB medium with ampicillin. DNAs prepared from these cultures were digested with BamHI and transformed into DH5α as described previously by Deng et al. (ibid.). In some cases, BamHI digestions were not complete, leading to a high percentage of DH5α transformants with nonmutant, BamHI-sensitive plasmids. DNA isolated from BMH 71-18 mut S is not digested to completion as readily as DNA isolated from DH5α or HB101. To reduce nonmutant background frequencies, a second round of BamHI selection was included in some experiments as follows. Plasmid DNA, prepared from greater than 1000 primary DH5α colonies, was digested with BamHI and retransformed into DH5α, yielding secondary DH5α transformants. Mutations were identified in plasmid DNAs isolated from both primary and secondary DH5α transformants by restriction mapping using BamHI, HindIII, and KpnI digestions.

Figure 6:
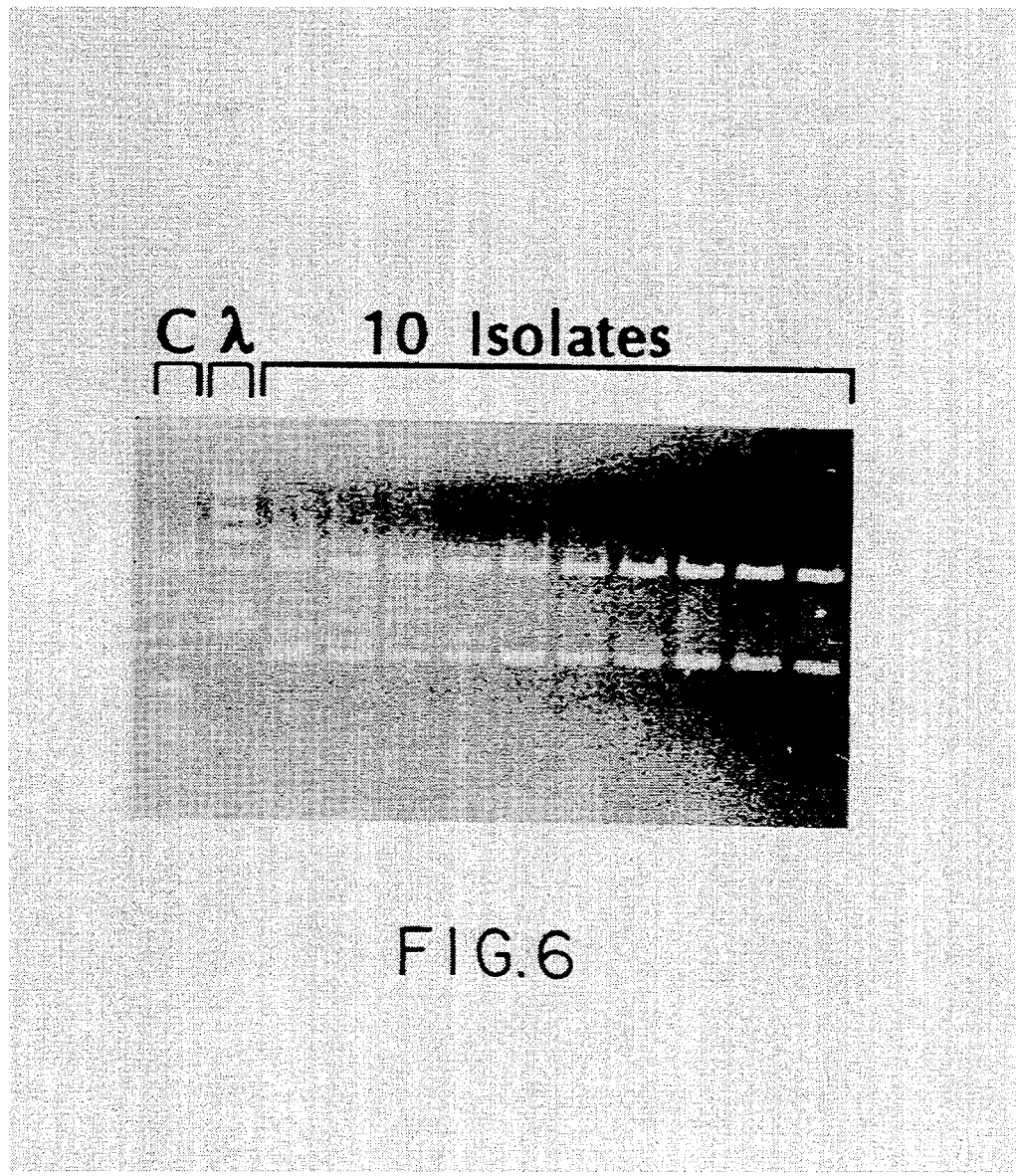
FIG. 6 is a photographic representation of an agarose gel of HindIII digests of pRSVEd1884 isolates following Long-Primer Unique Site Elimination Mutagenesis.

Nonselected mutants were isolated with high efficiency using the LP-USE procedure. Results of these experiments are shown in FIG. 6, and a summary of the results of two independent sets of LP-USE experiments are presented in TABLE 6.

TABLE 6

| Expt | Synthesis (min) | # Transformants BMH | # Transformants DH5α | Mutant Fraction-Primary DH5α BamHI | Mutant Fraction-Primary DH5α KpnI | Mutant Fraction-Primary DH5α HindIII | Mutant Fraction-Secondary DH5α BamHI | Mutant Fraction-Secondary DH5α KpnI | Mutant Fraction-Secondary DH5α HindIII |
|---|---|---|---|---|---|---|---|---|---|
| 1 | 5* | 420 | >1000 | 0/5 | ND | ND | 7/10 | 0/7 | 0/7 |
|   | 5 | 490 | >1000 | 3/5 | $R_3/3^R$ | 3/3 | 10/10 | 10/10 | 10/10 |
|   | 15 | 300 | >1000 | 0/5 | ND | ND | 5/10 | 0/5 | 0/5 |
|   | 30 | <10 | 1 | 1/1 | 1/1 | 0/1 | ND | ND | ND |
| 2 | 5* | 310 | >1000 | 0/24 | ND | ND | 0/10 | ND | 0/10 |
|   | 5 | 260 | >1000 | ND | ND | ND | 7/10 | 7/7 | 7/7 |
|   | 30 | 510 | >1000 | 10/24 | 10/10 | 0/10 | ND | ND | ND |

A 1498 bp fragment, amplified using primers 6B (BamHI) and 21A (HindIII), was used in LP-USE mutagenesis with second-strand synthesis reaction times ranging from 5 to 30 min. In reactions marked by (*), T4 DNA polymerase and T4 DNA ligase were omitted. The number of primary BMH 71-18 mut S transformants was estimated by plating aliquots of cells 1 hour after electroporation. For DH5, the entire transformation mixture was plated on a single plate. BamHI mutant fractions are given as the number of BamHI-resistant mutants/number of plasmids screened from primary or secondary DH5 colonies. KpnI and HindIII mutant fractions are given as the number of KpnI or HindIII mutants/BamHI-resistant mutants (except for , 10 BamHI-sensitive isolates were also tested for HindIII mutations).
ND = not determined.

The highest mutant yields were obtained with second strand synthesis reactions of 5 minutes. When both PCR product primers and T4 DNA polymerase were omitted, the BMH 71-18 mut S transformation frequency was reduced by more than 10-fold. When the PCR product was annealed, but in vitro second strand synthesis was omitted, BMH 71-18 mut S transformation frequencies were similar to those found when second strand synthesis was included. However, without in vitro synthesis, no BamHI-resistant mutants (or double mutants) were recovered from primary DH5α transformants. After a second round of BamHI selection was applied to pooled DNA isolated from DH5α transformants, BamHI-resistant mutants were recovered even in the absence of second strand synthesis. However, in this case, none of the BamHI-resistant mutants carried the nonselected HindIII mutation (TABLE 6, Experiment 2).

These same mutations were introduced by using the standard USE mutagenesis procedure. A total of 20 primary DH5α transformants were characterized. All 20 had BamHI-resistant/KpnI-sensitive mutations, and 16 of 20 carried the nonselectable HindIII mutation, yielding a mutagenesis efficiency of 80%.

5. Effects of PCR Product Length and Primer Separation Distance on the Efficiency of LP-USE and USE Mutagenesis In order to determine whether PCR product length or the distance separating primers influences LP-USE or USE mutagenesis efficiencies, respectively, these procedures were formed with 25 different pairs of primers, as described in Table 7.

TABLE 7

Effects of Primer Separation Distance on USE and LP-USE Efficiencies

| Primer Pair | Primer Separation (bp) | Linkage Fraction |
|---|---|---|
| LP-USE Procedure | | |
| 6B + 11 | 181 | ½ |
| 6B + 8 | 256 | ⅔ |
| 6B + 7 | 367 | 2/2 |
| 6B + 21A | 1469 | (see TABLE 6) |
| 6B + 17 | 1675 | 0/2 |
| 6B + 2 | 1948 | ½ |
| 6B + 13 | 1963 | 0/4 |
| 6B + 1 | 1966 | 0/6 |
| USE PROCEDURE | | |
| 6A + 11 | 181 | 1/1 |
| 6A + 9 | 253 | 2/5 |
| 6B + 10B | 247 | ⅔ |
| 6B + 12B | 532 | ¼ |
| 6A + 20 | 718 | 0/3 |
| 6B + 16B | 1339 | ½ |
| 6B + 15B | 1345 | ½ |
| 6A + 21A | 1469 | 16/20 |
| 6A + 17 | 1675 | 1/5 |
| 6B + 18B | 1837 | ½ |
| 6B + 19B | 1837 | 2/2 |
| 6B + 14B | 1900 | 2/2 |
| 6A + 3 | 1915 | 0/2 |
| 6B + 4B | 1912 | ½ |
| 6A + 5 | 1951 | 2/2 |
| 6A + 13 | 1963 | ⅔ |
| 6A + 1 | 1966 | 0/3 |

Each of the primers designed to introduce mutations into the T antigen gene were paired with either primer 6A or primer 6B (see Table 3), which were used to introduce the USE-and LP-USE-selectable mutations in the BamHI site.

Mutations introduced by all primers except 21A (SEQ ID NO:33), which eliminates a HindIII site, were identified by DNA sequence analysis. LP-USE second strand synthesis was performed for 30 minutes with all primers except primer 21A (SEQ ID NO:33) (see Table 6). Primer separation distances were measured from the position of the mutations. Linkage fractions indicate the number of nonselected mutants identified/number screened.

With both USE and LP-USE procedures, primer separation distances ranged from 181 to 1966 bp, and second strand synthesis reactions were incubated for 30 minutes. Nonselected mutations were identified for all primers except primer 21A (SEQ ID NO:33) by DNA sequence analysis of BamHI-resistant mutants since these mutations neither destroy nor create restriction sites.

The results of these experiments indicate that long PCR products are less effective as LP-USE mutagenic primers than small PCR products (see Table 7). However, it is important to note that the LP-USE experiments were performed with 30 minute incubations of second strand synthesis reactions, and that lengthy reactions were shown to reduce mutagenesis efficiency when the 1469 by PCR product of primers 6B and 21A was used. In contrast, there was no obvious relationship between primer separation distance mutagenesis efficiency when USE was employed. Note also that USE mutagenesis was not tested with synthesis reaction times below 30 minutes.

6. Fidelity of LP-USE and USE Mutagenesis

Since Tag DNA polymerase is known to produce high rates of misincorporation during PCR, tests were done to determine whether the addition of the PCR amplification step would result in an increase in the frequency of unwanted mutations. Approximately 200 bp of sequence information from each of 47 different plasmids screened for mutations in the T antigen gene was analyzed for the presence of unwanted mutations.

Figure 7:
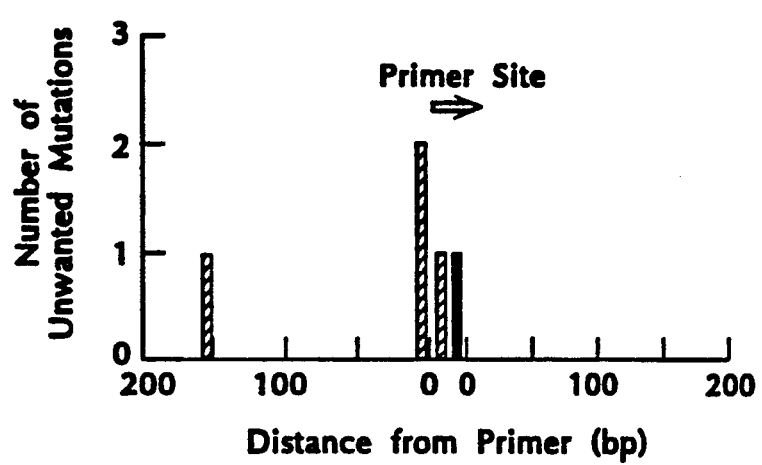
FIG. 7 is a graphic representation of the location of unwanted mutations following USE (hatched bars) and LP-USE (solid bars) mutagenesis relative to the position of nonselectable mutagenic primers.

This analysis indicated that unwanted mutations were introduced at comparable rates with both USE and LP-USE procedures. Only one unwanted mutation was found in 2690 bp following LP-USE mutagenesis, and four unwanted mutations were found in 6099 bp with USE, for an average rate of about 1:2200 bp. Although this rate might be expected to produce about one unwanted mutation in a gene of average size, it is important to note that most of the unwanted mutations were found very close to or within mutagenic primer sequences (see FIG. 7). In nearly 9000 sequenced base pairs, only one unwanted mutation was observed more than 150 bp from the primer site. Since the single unwanted mutation found with LP-USE was present within the primer sequence, and since unwanted mutations were also found within primer sequences following USE mutagenesis, this unwanted LP-USE mutation was probably not introduced during PCR amplification.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims.

---

We claim:

1. A method of producing mutant DNA, comprising the steps of:
   (a) generating from a circular parental DNA containing a nonessential, unique restriction site, circular mutant progeny DNA containing a desired mutation but lacking the restriction site, the progeny DNA being produced by a primer extension reaction wherein a primer carries the desired mutation;
   (b) treating the non-mutant parental DNA and the mutant progeny DNA with an enzyme that cleaves at the restriction site to cleave parental DNA such that enzyme cleavage at the restriction site linearizes parental DNA, while mutant progeny DNA remains circular; and
   (c) selecting for mutant progeny DNA by transforming mismatch repair-defective cells with the enzyme-treated DNA under conditions such that uncleaved DNA is transformed at a higher efficiency than cleaved DNA such that a majority of transformants carry mutant DNA.

2. A method of site-specific mutagenesis, comprising the steps of:
   (a) providing a circular, single-stranded DNA (ssDNA) containing both a nonessential, unique restriction site and a target DNA to be mutated;
   (b) providing a first oligonucleotide primer which is complementary to the target DNA but which contains a desired nucleotide mutation, and providing a second oligonucleotide primer complementary to the nonessential, unique restriction site of the same strand but which contains a nucleotide mutation in the site so that the site is eliminated;
   (c) annealing the first and second primers to the circular ssDNA under conditions which allow the first primer to hybridize to the target DNA and the second primer to hybridize to the unique restriction site;
   (d) synthesizing a new strand of DNA on the template of the circular ssDNA, the new strand lacking the unique restriction site and containing the mutation in the target DNA;
   (e) ligating the new strand of DNA to form a circular double-stranded DNA (dsDNA);
   (f) transforming a host cell which is mismatch repair-defective with the circular dsDNA;
   (g) culturing the cell to permit replication and cosegregation of the new strand of DNA so that circular dsDNA containing the primer-introduced mutation in both strands is produced;
   (h) isolating the circular dsDNA from the transformed, cultured host cell;
   (i) treating the isolated DNA with a restriction enzyme that cleaves the nonessential, unique restriction site so that parental-type circular DNA which contains the restriction site is cleaved to form linear DNA, but non-parental-type (mutant), circular DNA in which the restriction site has been eliminated is not cleaved and remains circular;
   (j) transforming a second host cell with the enzyme-treated DNA under conditions which allow the circular, mutant DNA to be taken up by the cells more efficiently than the linear, non-mutant DNA; and
   (k) culturing the transformed cells.

3. The method of claim 2, wherein the DNA containing the target DNA to be mutated is plasmid DNA, cosmid DNA, viral DNA, phagemid DNA or bacteriophage DNA.

4. The method of claim 3, wherein the DNA containing the target DNA to be mutated is selected from the group consisting of pUC19, pBR322, pBluescript TM, pBluescriptII TM, pSP6/T3, pSp6/T7-19, pT7/T3α-19 and pTZ19R.

5. The method of claim 4, wherein the second oligonucleotide primer is selected from the primers listed in the Sequence Listing as SEQ ID NOS:1–33, or their complements.

6. The method of claim 2, wherein the second primer creates a new and different restriction site.

7. The method of claim 2, wherein the new strand of DNA is synthesized by extending DNA from the first and second primers using T4 polymerase, followed by ligation with T4 ligase.

8. The method of claim 2, wherein the mismatch repair-defective cell line is *E. coli* strain BMH 71-18 rout S.

9. The method of claim 2, wherein the cells are transformed by electroporation.

10. A method of site-specific mutagenesis, comprising the steps of:
  (a) providing a circular double-stranded DNA containing both a nonessential, unique restriction site and a target DNA to be mutated;
  (b) providing a first oligonucleotide primer which is complementary to the target DNA of one strand but which contains a desired nucleotide mutation, and providing a second oligonucleotide primer complementary to the nonessential, unique restriction site of the other strand but which contains a nucleotide mutation in the site so that the site is eliminated;
  (c) denaturing the circular dsDNA to form circular ssDNA, or denaturing a linear dsDNA fragment to form linear ssDNA;
  (d) annealing the first and second primers to the ssDNA under conditions which allow the first primer to hybridize to the target DNA of one strand and the second primer to hybridize to the other strand at the unique restriction site;
  (e) performing a polymerase chain reaction (PCR) under conditions sufficient to produce a linear dsDNA product containing the mutation in the target DNA but lacking the restriction site;
  (f) denaturing the ds product to generate linear ssDNA;
  (g) annealing the linear ssDNA to the circular ssDNA;
  (h) synthesizing a new strand of DNA on the template of the circular ssDNA;
  (i) ligating the new strand of DNA to form a circular double-stranded DNA (dsDNA), the new strand lacking the unique restriction site and containing the mutation in the target DNA;
  (j) transforming a host cell which is mismatch repair-defective with the circular dsDNA;
  (k) culturing the transformed cell to permit replication of the new strand so that circular dsDNA containing the primer-introduced mutation in both strands is produced;
  (l) isolating the circular dsDNA from the transformed, cultured host cell of step (k);
  (m) treating the isolated DNA with a restriction enzyme that cleaves the nonessential, unique restriction site so that parental-type circular DNA which contains the restriction site is cleaved to form linear DNA, but non-parental-type (mutant), circular DNA in which the restriction site has been eliminated is not cleaved and remains circular;
  (n) transforming a second host cell with the enzyme-treated DNA under conditions which allow the circular, mutant DNA to be taken up by the cells more efficiently than the linear, non-mutant DNA; and
  (o) culturing the transformed cells.

11. The method of claim 10, wherein the circular ssDNA containing the target DNA to be mutated is plasmid DNA.

12. The method of claim 11, wherein the plasmid DNA is selected from the group consisting of pUC19, pBR322, pBluescript TM, pBluescriptII TM, pSP6/T3, pSP6/T7-19, pT7/T3α-19 and pTZ19R.

13. The method of claim 12, wherein the second oligonucleotide primer is selected from the primers listed in the Sequence Listing as SEQ ID NOS:1–33.

14. The method of claim 10, wherein the second primer creates a new restriction site.

15. The method of claim 10, wherein the new strand of DNA is synthesized by extending DNA from the first and second primers using T4 polymerase followed by ligation with T4 ligase.

16. The method of claim 10, wherein the mismatch repair-defective cell line is *Escherichia coli* strain BMH 71-18 mut S.

17. The method of claim 10, wherein the cells are transformed by electroporation.

18. A kit for performing site-directed mutagenesis of circular DNA, comprising:
  (a) a bacterial host cell which is mismatch repair-defective;
  (b) an oligonucleotide primer which is complementary to a nonessential, unique restriction site of the DNA but which contains a nucleotide mutation in the site so that the site is eliminated; and
  (c) circular control DNA which contains a nonessential, unique restriction site and a mutation in an indicator gene so that the indicator gene is inactive.

19. The kit of claim 18, further comprising:
  (a) a DNA polymerase capable of directing second strand DNA synthesis from a primer and a DNA ligase;
  (b) deoxyribonucleotides including deoxyadenosine 5'-triphosphate, deoxyguanosine 5'-triphosphate, deoxycytosine 5'-triphosphate, and thymidine 5'-triphosphate;
  (c) a restriction enzyme for cleaving the unique restriction site;
  (d) ATP (adenosine 5'-triphosphate) and a polynucleotide kinase;
  (e) reagents to enhance DNA synthesis in vitro;
  (f) buffers for performing phosphorylation reactions, PCR reactions, DNA synthesis reactions, restriction enzyme digestions, and DNA purification; and
  (g) control primers for monitoring mutagenesis efficiencies.

20. The kit of claim 18, wherein the DNA is plasmid DNA.

21. The kit of claim 18, wherein the mismatch repair-defective host is *Escherichia coli* strain BMH 71-18 mut S.

22. The kit of claim 19, wherein the DNA polymerase is T4 DNA polymerase and the ligase is T4 DNA ligase.

23. The kit of claim 19, wherein the polynucleotide kinase is T4 polynucleotide kinase.

24. The kit of claim 19, wherein the reagent for enhancement of DNA synthesis is T4 gene 32 protein.

25. The kit of claim 19, wherein a first control primer eliminates the mutation in the indicator gene of the control plasmid, thereby restoring gene activity and a second control primer eliminates the nonessential, unique restriction enzyme recognition site of the control plasmid.

26. A method of claim 1, for targeted rescue of a mutant DNA, wherein a primer containing a mutant gene to be rescued is used to generate the progeny DNA.

27. A method of claim 1, wherein the parental DNA is double-stranded.

28. The method of claim 2 further comprising isolating the circular dsDNA from the transformed host cell, the majority of the isolated circular dsDNA containing the mutation in the target DNA.

29. The method of claim 2 further comprising providing in step (b) multiple oligonucleotide primers which are complementary to the target DNA but contain desired mutations to produce multiple mutations simultaneously.

30. The method of claim 28 further comprising providing in step (b) multiple oligonucleotide primers which are complementary to the target DNA but contain desired mutations to produce multiple mutations simultaneously.

31. The method of claim 10 further comprising isolating the circular dsDNA from the transformed host cell, the majority of the isolated circular dsDNA containing the mutation in the target DNA.

* * * * *

UNITED STATES PATENT AND TRADEMARK OFFICE
CERTIFICATE OF CORRECTION

PATENT NO. : 5,354,670
DATED : October 11, 1994
INVENTOR(S) : Jac A. Nickoloff et al.

It is certified that error appears in the above-indentified patent and that said Letters Patent is hereby corrected as shown below:

In column 2, line 36, replace "uncleared" with -- uncleaved --;

In column 3, line 64, replace "rout S" with -- mut S --;

In column 4, line 17, replace "vital" with -- viral --;

In column 4, line 43, replace "Any E. Coli" with -- Any E. coli --;

In column 9, Table 2, insert -- (SEQ ID NO:1) -- after " 5'-CACCACGATGCCTGCAGCAATGGCAAC-3' ";

In column 10, Table 2, insert -- (SEQ ID NO:2) -- after " 5'-CAGGTTCTCCTGCAGCTTGGGTGG-3' ";

In column 17, Table 6, line 15, replace "0/10" in the last HindIII column with -- 0/10† --; and In column 17, in the legend for Table 6, line 24, replace "(except for , 10 BamHI-sensitive isolates were ND = not determined)" with -- (except for †, 10 BamHI-sensitive isolates were ND = not determined) --.

UNITED STATES PATENT AND TRADEMARK OFFICE
CERTIFICATE OF CORRECTION

PATENT NO. : 5,354,670
DATED : October 11, 1994
INVENTOR(S) : Jac A. Nickoloff et al.

It is certified that error appears in the above-indentified patent and that said Letters Patent is hereby corrected as shown below:

In claim 1, column 35, lines 41-42, replace "a desired mutation but lacking the restriction site" with -- both a desired mutation and a mutation that eliminates the restriction site --;

In claim 8, column 37, line 19, replace "E. coli strain " with -- Escherichia coli strain --;

In claim 8, column 37, line 20, replace "rout S" with -- mut S --;

In claim 18, column 38, line 39, insert -- circular -- before "DNA" and -- to be mutagenized -- after "DNA";

In claim 28, column 39, line 18, replace "host cell" with -- cells of step (k) --;

In claim 31, column 40, line 15, replace "host cell" with -- cells of step (o) --;

Signed and Sealed this

Twenty-fourth Day of January, 1995

Attest:

BRUCE LEHMAN

*Attesting Officer*    *Commissioner of Patents and Trademarks*